United States Patent
Rorberg et al.

(10) Patent No.: US 8,138,991 B2
(45) Date of Patent: Mar. 20, 2012

(54) REAL-TIME IMAGE SCANNING AND PROCESSING

(75) Inventors: Eli Rorberg, Haffa (IL); Yoav Ophir, Zichron Ya'acov (IL); Asaf Bloch, Shimahit (IL)

(73) Assignee: Elbit System Ltd., Haifa (IL)

( * ) Notice: Subject to any disclaimer, the term of this patent is extended or adjusted under 35 U.S.C. 154(b) by 1033 days.

(21) Appl. No.: 11/644,821

(22) Filed: Dec. 22, 2006

(65) Prior Publication Data

US 2010/0141555 A1 Jun. 10, 2010

(30) Foreign Application Priority Data

Dec. 25, 2005 (IL) .......................................... 172797

(51) Int. Cl.
*G09G 5/00* (2006.01)

(52) U.S. Cl. ............ 345/8; 345/634; 345/637; 345/638; 345/643

(58) Field of Classification Search .................. 345/7–9, 345/609, 1.1, 634, 637–638, 643; 349/11, 349/13
See application file for complete search history.

(56) References Cited

U.S. PATENT DOCUMENTS

| | | | |
|---|---|---|---|
| 4,682,160 A * | 7/1987 | Beckwith et al. | 345/421 |
| 5,040,058 A | 8/1991 | Beamon, III | |
| 5,301,038 A * | 4/1994 | Todd | 382/269 |
| 5,880,777 A | 3/1999 | Savoye et al. | |
| 6,417,866 B1 * | 7/2002 | Man et al. | 345/660 |
| 6,466,226 B1 * | 10/2002 | Watson et al. | 345/610 |
| 6,867,537 B2 | 3/2005 | Sato et al. | |
| 2002/0075286 A1 * | 6/2002 | Yonezawa et al. | 345/679 |
| 2003/0107770 A1 * | 6/2003 | Klatchko et al. | 358/3.21 |
| 2004/0169617 A1 * | 9/2004 | Yelton et al. | 345/1.1 |

* cited by examiner

*Primary Examiner* — Amr Awad
*Assistant Examiner* — Kenneth Bukowski
(74) *Attorney, Agent, or Firm* — Lathrop & Gage LLP

(57) ABSTRACT

An apparatus for displaying at least one image with respect to a line-of-sight (LOS), with an image source, a display processor and a displaying unit. The display processor is coupled with the image source and the displaying unit. The image source provides at least one spatially unregistered image, and the display processor spatially registers the spatially unregistered image with the LOS, thereby generating a respective at least one spatially registered image. The displaying unit displays at least one spatially registered pixel on a displaying surface. The display processor includes a storage unit, an image processor and a pixel locator, the pixel locator being coupled with the image processor, wherein the storage unit stores the spatially unregistered image. The image processor selects at least one projection pixel to be displayed and the pixel locator determines, in each spatially unregistered image, the location of the spatially registered pixel corresponding to the selected projection pixel.

62 Claims, 10 Drawing Sheets

REAL-TIME IMAGE SCANNING AND PROCESSING

RELATED APPLICATIONS

This application claims priority to Israeli Patent Application No. 172797, filed Dec. 25, 2005, the disclosure of which is incorporated herein by reference.

FIELD OF THE DISCLOSED TECHNIQUE

The disclosed technique relates to spatial registration and event latency in general, and to methods and systems for processing and scanning image data with minimal image latency, in particular.

BACKGROUND OF THE DISCLOSED TECHNIQUE

The vestibulo-ocular reflex (herein abbreviated VOR) is a reflex of the human eye whereby head movement causes movement of the eyes in an opposite direction (i.e., to that of the head). As the head moves, the semicircular canals in the ears, which are spatially located in three perpendicular planes, send signals to the brain indicative of the velocity and acceleration of the head in all directions. The brain then sends signals to the muscles of the eye to move in an opposite direction to the direction of head movement. The VOR results in a stabilized image on the retina of the eye as the head moves and allows the eyes to stay aligned and focused on an object even as the head moves.

Reference is now made to FIG. 1A, which is an illustration of the vestibulo-ocular reflex, as is known in the art. In FIG. 1A, a person in position 10, is looking with his eye 20, at an object 12. The person in position 10 has a line-of-sight (herein abbreviated LOS) depicted by arrow 26 (It is noted that in FIGS. 1A-1D, lines-of-sight will be depicted by double head arrows, whereas light rays directed towards the eye of a person will be depicted by single head arrows). As the person moves his head up from position 10, represented by position 16, and down, represented by position 18, due to the VOR, his eyes move in an opposite direction to the movement of his head in order to keep his LOS directed towards object 12. For example, in position 16, where the person has his head up, his eye 22 is looking down, such that his LOS 28 stays aligned on object 12. In position 18, where the person has his head down, his eye 24 is looking up, such that his LOS 30 stays aligned on object 12. Because of the VOR, the person will see a stabilized image 14 of object 13, which is in focus and is not blurred, jittered or vibrated. It is noted that the VOR is a fast human reflex, has a response time of less than 10 milliseconds, and can stabilize images on the retina of the eye for changes in head velocity of up to 500 degrees per second. Since the VOR is a fast reflex, the brain of a person generally expects images perceived by the eyes to be stabilized on the retina, (i.e. as the head moves, images perceived by the eyes do not move). This general expectation can be termed "real world behavior" as images perceived by the eyes of a person which originate from the real world (as opposed to those generated or produced by a video system) are usually stabilized.

Reference is now made to FIG. 1B, which is another illustration of the vestibulo-ocular reflex, as is known in the art. In FIG. 1B, a person in position 50 is looking with his eye 70 at an object 52, along a LOS 76. A projection unit 56, which can be, for example, a heads-up display (herein abbreviated HUD), also projects an image to eye 70. The image may be, for example, a firing crosshair, altitude levels of an aircraft or any other known symbology projected to an operator of a vehicle. The image projected to eye 70 from projection unit 56 is superimposed on the image eye 70 sees along LOS 76. It is noted that projection unit 56 is not physically attached to the person. Projection unit 56 projects the image along an axis 82 towards a mirror 57, which has been treated with a semi-reflective treatment making mirror 57 a combiner, as is known in the art. The semi-reflective treatment enables eye 70 to see an image projected onto mirror 57 as well as images located beyond mirror 57.

When the image impinges on mirror 57, the image is directed towards eye 70 along an axis 84. As the person in position 50 moves his head up, represented by position 66, and down, represented by position 68, due to the VOR, the eyes of that person move in an opposite direction to the movement of his head, in order to keep his LOS directed towards object 52. For example, the person in position 66, who has his head up, has his eye 72 looking down, such that his LOS 78 stays aligned on object 52. And person in position 68, who has his head down, has his eye 74 looking up, such that his LOS 80 stays aligned on object 52. Since the image projected along axis 82 impinges mirror 57 at a particular location, then as the person in positions 66 and 68 looks through mirror 57 towards object 52, in each position he will see the image projected from projection unit 56 along a particular axis, respectively an axis 78 and an axis 80. Due to the VOR, the image from projection unit 56 will also be stabilized on the retina. Therefore, the image 54 seen by the person will be stabilized, such that an object 64 is seen in focus, and images projected from projection unit 56 will also be seen in focus, such as a crosshair 60, a target marker 62 and a level indicator 58.

Reference is now made to FIG. 1C, which is a further illustration of the vestibulo-ocular reflex, as is known in the art. In FIG. 1C, a person in position 100 is looking with his eye 108 at an object 112, along a LOS 110. The person is wearing a helmet 102. Helmet 102 includes a projection unit 104, which is physically coupled with the helmet, and a visor 106, which has been treated with a semi-reflective treatment making visor 106 a combiner, as is known in the art. Projection unit 104 and visor 106 are collectively referred to in the art as a helmet mounted display (herein abbreviated HMD). Projection unit 104 can project an image to the eye along an optical path 111 towards eye 108. The image may be, for example, a firing crosshair, altitude levels of an aircraft or any other known symbology projected to an operator of a vehicle.

As the person in position 100 moves his head up, represented by position 118, and down, represented by position 132, due to the VOR, his eyes move in an opposite direction to the movement of his head in order to keep his LOS directed towards object 112. For example, the person in position 118, who has his head up, has his eye 128 looking down, such that his LOS 130 stays aligned on object 112. And the person in position 132, who has his head down, has his eye 142 looking up, such that his LOS 144 stays aligned on object 112. Since projection unit 104 is coupled with helmet 102, and therefore moves as the person moves his head, the image projected along axis 111 will move with his head and will appear blurred on the retina of eye 108. For example, since the person in position 118 moves his head up, and therefore instinctively turns his eye 128 down to stay aligned on object 112, projection unit 122 projects an image along an optical path 126, which is reflected by a visor 124 and impinges on the upper part of the retina of eye 128. And since the person in position 132 moves his head down, and therefore instinctively turns his eye 142 up to stay aligned on object 112, projection unit 136 projects an image along an optical path 140, which is reflected by a visor 138 and impinges on the lower part of the retina of eye 142.

As a result of the VOR, the image 114 seen by eye 108 will be partially stabilized. Object 116 will be in focus, as the VOR adjusts the LOS of eye 108 such that it always stays aligned on object 112. Nevertheless, since projection unit 104 moves as the person moves his head, a level indicator 146, a crosshair 148 and a target marker 150 will also move with his head since the optical path from the projection unit towards the eye will not coincide with the optical path the eye will look at as it stays aligned on object 112. This will result in level indicator 146, crosshair 148 and target marker 150 appearing blurred on the retina of the eye. It is noted that this was not the case in FIG. 1B, where the optical path the eye will look at, as it stays aligned on object 52, coincides with the optical path along which projection unit 56 provides an image. Another reason why the symbology appears blurred on the retina of the eye is that the person expects real world behavior regarding level indicator 146, crosshair 148 and target marker 150. Since the VOR of the person instinctively moves his eyes, which are looking at object 112, in an opposite direction to the direction of movement of his head, the symbology projected onto visor 106 will not be stabilized by the VOR. In effect, the symbology projected onto visor 106 will move as the head of the person moves from position 100 to positions 118 and 132 respectively. Therefore such symbology will not be perceived as other images are normally perceived in the real world, for example object 112, which results in a perceived symbology which is blurred or jittered. Blurred symbology perceived by the eye of the person can also cause undesirable effects, such as motion sickness and making sighting, targeting and aiming a weapon very difficult Reference is now made to FIG. 1D, which is another illustration of the vestibulo-ocular reflex, as is known in the art. In FIG. 1D, a person in position 180 is looking with his eye 188 at a projected image of object 192, along a LOS 190. Person 180 is wearing a helmet 182. Helmet 182 includes a projection unit 184, which is physically coupled with the helmet, and a visor 186, which has been treated with a semi-reflective treatment making visor 186 a combiner, as is known in the art. Projection unit 184 can project an image to the eye along an optical path 191 towards eye 188. The image may be, for example, a firing crosshair, altitude levels of an aircraft or any other known symbology projected to an operator of a vehicle. Since the outside scene seen by the person in position 180 is dark, and as such, eye 188 cannot perceive it, projection unit 184 also projects a light intensified image of object 192. The light intensified image can also be a FLIR (forward looking infrared) image, an ICCD (intensified charge coupled device) image, a night vision image and the like.

As the person in position 180 moves his head up, represented by position 198, and down, represented by position 212, since the only image the person perceives is the image projected onto visor 186, the person will move his eyes in accordance with the movements of his head to keep his eyes aligned on the light intensified image of object 192. For example, the person in position 198, who has his head up, has his eye 208 looking up, such that his LOS 210 stays aligned on the projection of object 192 onto his visor 204. The person in position 212, who has his head down, has his eye 222 looking down, such that his LOS 224 stays aligned on the projection of object 192 onto his visor 218. Since projection unit 184 is coupled with helmet 182, and therefore moves as the person moves his head, the image projected along axis 191 will move with his head. Since the projected image moves with the movement of the head of the person, the projected image will not be stabilized on the retina of the eye. As mentioned with reference to FIG. 1C, a person expects real world behavior from images perceived by the eyes, whether they be from the real world or from a video system. In FIG. 1D, the VOR cannot stabilize the image projected onto visor 186 as the image itself is constantly moving in accordance with movements of the head.

As a result, object 196, which is projected from projection unit 184, will be out of focus, blurred and jittered, as the VOR cannot adjust the LOS of eye 188 such that it always stays aligned on a fixed projected image of object 192 which is itself constantly moving. Also, since projection unit 184 moves as the person moves his head, a level indicator 226, a target marker 228 and a crosshair 230 also will be seen as blurred. It is noted that in the imaging situation of FIG. 1D, where an operator of a vehicle "sees" via a projected image onto his eye and not by direct sight, the image projected to the eye of the operator can cause undesirable effects, such as motion sickness and sighting, targeting and aiming a weapon very difficult. In particular, when the scene seen by the operator is dark, the chance of motion sickness in the operator is increased, since the operator expects his VOR to stabilize the projected image. As explained below, his VOR will, in practice, not be able to stabilize the projected image, and therefore, since the image will be blurred, the chance of motion sickness increases.

In the imaging situation of FIG. 1D, since the image projected onto visor 186 does not remain still, the VOR of the person cannot stabilize the image of object 192. Furthermore, in practice, since the person may be in a vehicle, for example, an aircraft, which vibrates and resonates (due to, for example, air gusts passing the aircraft and the engine of the aircraft), then even if he does not move his head, and his eyes stay focused and aligned on visor 186, the image projected thereon will still appear blurred due to the movements and vibrations of the vehicle. In order to stabilize the blurred image, systems and methods have been devised to mimic the image stabilization process of the VOR in the image projected onto a visor, as is illustrated in FIGS. 2, 3A and 3B. In such systems and methods, the movement of the head of the pilot (for example, the azimuth, elevation and rotation of the head, the location of the head in the reference frame of the aircraft, the speed and the acceleration at which the head is moving) as well as the movement of the aircraft, are measured. In accordance with those measurements, the image provided to the pilot is modified and processed such that it is presented to the pilot in a constant and fixed position, as if the image did not move with the movements of the head of the pilot. By constantly updating the image such that it is placed in a fixed position relative to the pilot allows the VOR of the pilot to stabilize the image the pilot sees as his head moves around. In general, in the art, the process of modifying an image and processing it such that it is presented to an operator of a vehicle in a constant, fixed position (even though the head of the operator moves vis-à-vis the surface onto which the image is projected), or at the correct spatial location such that the operator will see a stabilized image, is known as spatial registration.

Reference is now made to FIG. 2, which is a schematic illustration of a prior art airborne vision and imaging system, generally referenced 250. System 250 includes a camera 252, a head sensor 254, an inertial navigation system (herein abbreviated INS) 256, a vehicle motion system 258, a display processor 260 and a projection unit 262. INS 256 is coupled with vehicle motion system 258. Head sensor 254, camera 252 and vehicle motion system 258 are each coupled with display processor 260, which is in turn coupled with projection unit 262. Camera 252 may be, for example, an IR camera, a visible light camera and the like. Camera 252 can also be an image generator which can generate virtual reality images. The image received by camera 252 may be light intensified, infrared images, ICCD images, or otherwise images not normally visible to the human eye. If camera 252 is an image generator, then camera 252 generates virtual reality images, for example, of a virtual world. Head sensor 254 is located on the helmet of the pilot (not shown) and measures the movement (e.g., azimuth, elevation, rotation and location of the helmet in the reference frame of the aircraft, as well as the velocity and acceleration of the helmet) of the head of the pilot in all directions. INS 256 is located on the aircraft (not shown), and measures the movement of the aircraft in all directions. Vehicle motion system 258 monitors the position of the aircraft, the movement of the aircraft in all directions, as well as other systems related to the aircraft, such as general avionics, weapons system, a fuel system and the like. Projection unit 262 is located on the helmet of the pilot, which is equipped with an HMD, and projects an image received from camera 252, and any other data provided by vehicle motion system 258, onto the visor of the helmet.

Camera 252 receives an image of an outside scene. If camera 252 is an image generator, then camera 252 generates an image of an outside scene. The image may be an IR image, an ICCD image, or it may be light intensified. Camera 252 provides the image to display processor 260. Head sensor 254 continuously measures the movement of the head of the pilot and provides these measurements to display processor 260. INS 256 continuously measures the movement of the aircraft and provides these measurements to vehicle motion system 258, which in turn provides them to display processor 260. Vehicle motion system 258 can also provide display processor 260 with other data regarding the aircraft, for example, the altitude of the aircraft, the LOS of the weapons system, the amount of fuel left in the aircraft, and the like.

Display processor 260 receives the image captured by camera 252 and corrects the image for any distortion (for example, pincushion distortion or barrel distortion) it may have due to the optics of the camera. If camera 252 is an image generator, then no correction for distortion needs to be executed. Display processor 260 also receives measurements of the movement of the head of the pilot (which is indicative of his LOS) as well as measurements of the movement of the aircraft. Display processor 260 uses both of these measurements to modify and process the image captured, or generated, camera 252. For example, if the aircraft is in a turn maneuver, and the body of the aircraft forms a 45° angle with respect to the horizon, and the pilot has his head angled at a −25° angle with respect to the horizon, then helmet display processor may scale, shift, rotate and crop the image captured, or generated, from camera 252 such that it is placed at the correct spatial location on the visor of the helmet such that it coincides with a fixed and constant position relative to the pilot. Furthermore, if the pilot lifts his head, then display processor 260 may shift the image captured, or generated, from camera 252 down to keep the image in at the fixed position relative to the pilot. It is furthermore noted that the position of the head of the pilot can be predicted by known head movement prediction algorithms and that these predicted positions can be used to modify and process the image such that it stays in the fixed position relative to the pilot (i.e., the image is spatially registered correctly). By keeping the image projected from camera 252 in a fixed position, the VOR of the pilot can stabilize the image on the retina of the eye as the pilot moves his head.

Display processor 260 can also superimpose aircraft symbology, as well as other data, such as a digital map, over the image captured, or generated, from camera 252. It is noted that in the case of a digital map, the digital map image may be superimposed over the image captured, or generated, by the camera in a picture-in-picture (herein abbreviated PIP) format. It is also noted that the symbology, as well as other data, may need to be processed, like the image captured, or generated, from camera 252 was processed, such that it coincides with the fixed position relative to the pilot when that other data is projected onto the visor of the helmet.

Since the visor of the pilot is curved, and the projection unit may contain particular optical elements that distort the projected image, any image projected onto the visor needs to be correctly distorted such that the distortion in the image caused by the projection unit is corrected for and the projected image is seen properly on the curved visor. After display processor 260 has finished processing the original image captured, or generated, by camera 252, which can include, as mentioned above, scaling, cropping, rotating and shifting the image, as well as superimposing other images on the original image, display processor 260 then distorts the image such that it can be presented to the pilot on his visor without distortions. Display processor 260 then provides the processed, distorted image to projection unit 262 which projects the image to the visor of the pilot.

Reference is now made to FIGS. 3A and 3B. FIG. 3A is a schematic illustration of a prior art method for spatial registration. FIG. 3B is a graphical representation of the method of 3A. In procedure 280, a raw image is received from a camera, or generated by an image processor. The image may be, for example, a light intensified image, an IR image, an ICCD image, or a FLIR image. Due to the optics of the camera that received the image, the image may be distorted. If the raw image is a virtual world image generated by an image processor, then the raw image will not be distorted. With reference to FIG. 3B, an image 320 represents a raw image received from a camera, or generated by an image processor. It is noted that image 320 can be distorted due to the optics of the camera. In procedure 282, aircraft data as well as head sensor data is received. Aircraft data can include measurements of the aircraft heading, direction, velocity and acceleration as well as information such as the altitude of the aircraft, the LOS of the weapons system, the amount of fuel remaining in the aircraft, and the like. Head sensor data can include measurements of the movement of the head of the pilot in all directions (e.g., azimuth, elevation, rotation and location in the reference frame of the aircraft, as well as velocity and acceleration).

In procedure 284, the image received from the camera is corrected for distortions. Since the image received from the camera will be processed and manipulated, distortions in the image must be initially corrected before the image is processed, otherwise each manipulation to the image will further distort the original image and the final image will be even further distorted. If the image was generated by an image processor, then no distortion correction needs to be executed. With reference to FIG. 3B, an image 322 represents the distortion-corrected image of raw image 320. In procedure 286, symbology representing information regarding the aircraft is generated. The symbology is generated based on the aircraft data received in procedure 282. With reference to FIG. 3B, an image 324 represents the symbology generated in accordance with the aircraft data received. In procedure 288, a digital map, showing the location of the aircraft, is generated in accordance with the aircraft data received in procedure 282. The digital map will be displayed to the pilot in a PIP format. With reference to FIG. 3B, an image 326 represents a digital map generated in accordance with the aircraft data received.

In procedure 290, the distortion-corrected image of procedure 284 is processed in accordance with the aircraft data and head sensor data such that it will be spatially registered correctly. For example, the processing may include scaling, shifting, cropping and rotating the image, all in accordance with the heading of the aircraft and the head position of the pilot. The processing may also include image processing such as brightness correction, gamma correction and the like. With reference to FIG. 3B, an image 328 represents a scaled, shifted, rotated and cropped version of image 322. Image 328 has been processed in accordance with the aircraft data and the head sensor data to keep the projected image in a fixed position relative to the pilot. In procedure 292, the symbology generated in procedure 286 is processed in accordance with the aircraft data and head sensor data such that it will be spatially registered correctly. With reference to FIG. 3B, an image 330 represents a scaled, shifted, rotated and cropped version of image 324. In procedure 294, the digital map generated in procedure 288 is processed in accordance with the aircraft data and head sensor data such that it will be spatially registered correctly. With reference to FIG. 3B, an image 332 represents a scaled, shifted, rotated and cropped version of image 326. In general, it is noted that the procedures of processing the distortion-corrected camera image, the symbology and the digital map can be executed in parallel.

In procedure 296, the camera image, the symbology and the digital map are fused into a single image. The fusion can be executed by superimposing the symbology over the camera image and inserting the digital map over a portion of the camera image in a PIP format. With reference to FIG. 3B, an image 334 represents a fused version of image 328, image 330 and image 332. In procedure 298, the fused image is stored and recorded. With reference to FIG. 3B, an image 336 represents a stored and recorded version of image 334. It is noted that image 334 has been cropped to form image 336. In procedure 300, the fused image of procedure 296 is processed such that it can be projected to each eye of the pilot and stored in memory. The processing can include properly distorting the fused image, for each eye, such that it will be correctly displayed on the visor of the helmet, which is a curved surface having an inherent distortion. The processing can also include correcting any distortion due to the optics of an image projector which projects the image on the visor of the helmet. With reference to FIG. 3B, an image 338 represents a stored right-eye distorted version of image 334, and an image 340 represents a stored left-eye distorted version of image 334. Each of images 338 and 340 has been distorted in accordance with the inherent distortion of the visor of the helmet, and the image projector, such that the image will appear undistorted when projected onto the visor. In procedure 302, the stored processed fused image of each eye is respectfully projected to each eye of the pilot via the visor of the helmet of the pilot. With reference to FIG. 3B, it is noted that images 338 and 340 are first stored in memory before they are projected to the eyes of the pilot.

In general, in airborne imaging and vision systems, the refresh rate of the projection unit is approximately 60 Hz. Therefore, it takes approximately 16.6 milliseconds for the projection unit to generate an entire image to be projected to a pilot. Furthermore, according to the system and method described above, with reference to FIGS. 2, 3A and 3B, each time an image, whether it be the camera image, the symbology or the digital map, is modified (e.g., cropped, rotated, distortion-corrected and the like), the modified image is stored in memory. Storing the image in memory can be a time costly process, as tens of milliseconds may be needed to store the image, depending on the speed of the memory hardware, the data buses, the image resolution, the update rate of the head sensor data and aircraft data, which can be 30 Hz, for example, and the like. Referring back to FIG. 3B, considering images 320, 324 and 326 are stored in memory, then image 322 is stored in memory, then images 328, 330 and 332 are stored in memory, then image 334 is stored in memory, then images 338 and 340 are stored in memory and finally images 338 and 340 are then projected to the eyes of the pilot, the procedure of spatially registering the image projected to the eyes of the pilot in accordance with the movements of the head of the pilot and the movements of the aircraft can take over 100 milliseconds. At this pace, conventional projection units update the image data projected to the pilot at a typical rate of approximately 10 Hz, a rate significantly lower than the refresh rate of the projection unit, and a rate significantly slower than the VOR of humans. At such rates, the image and the information presented to the pilot may not be current and up-to-date, and the VOR may not be able to properly stabilize the image, since the reflex operates at a rate faster than the update rate of the image.

Systems using the method described in FIGS. 3A and 3B therefore exhibit a significant latency in terms of spatial registration and event registration. Event registration refers to the amount of time required for a camera to capture an event, for example, an explosion, and transmit the explosion graphically to the eye of the pilot via a projection unit. Event registration can also refer to the amount of time required for an image generator to receive data regarding a new object in the image and to generate the new object on the image. Event registration can further refer to the amount of time required to update flight symbols projected to the eyes of the pilot.

U.S. Pat. No. 6,867,753 to Chinthammit et al., entitled "Virtual image registration in augmented field display" is directed to a system for registering a virtual image on a perceived real world background. A tracking light is scanned in the real world environment. Light is detected as it impinges on a pair of detector surfaces of a first detector, at a first time and at a second time, when the first time and second time occur within adjacent scan lines. The time at which a horizontal scan line edge is encountered is derived as occurring half way between the first time and the second time. The horizontal location of the first detector is then determined within a specific scan line which is derived from the scan line edge time. The vertical location of the detector is then determined within a scan frame by measuring the time duration using the beginning of the frame. The location of the detector surfaces is thus determined independently from the temporal resolution of the augmented imaging system at a sub-pixel/sub-line resolution. The augmented image is registered to a 3D real world spatial coordinate system based upon the tracked position and orientation of a user. Prediction algorithms are used to compensate for the overall system latency.

U.S. Pat. No. 5,040,058 to Beamon et al., entitled "Raster graphic helmet mountable display" is directed to a helmet mountable display for supplying a full color image for presentation to a wearer of the helmet. An electronic apparatus, for example, a cathode ray tube, having red, green and blue strips of emitting phosphors, along with an electron gun, for scanning a trace in each strip, provides sweep lines for a full color raster graphic image. An electromechanical apparatus disposes the sweep lines to appear at their proper spatial position on the image. Registration and superposition of the traces are executed by a color information delay apparatus and a focusing optical system, which form a sweep line exhibiting full color characteristics which form a portion of the image.

U.S. Pat. No. 5,880,777 to Savoye et al., entitled "Low-light-level imaging and image processing" is directed to an imaging system for producing a sequence of image frames of an imaged scene at a frame rate R, which is a rate of at least 25 image frames per second. The imaging system includes an analog-to-digital processor for digitizing an amplified pixel signal to produce a digital image signal. Each digital image signal is formatted as a sequence of image frames, with each image frame having a plurality of digital pixel values. The digital pixel values have a dynamic range of values which are represented by a number of digital bits B, with B being greater than 8. The imaging system also includes a digital image processor, for producing an output image frame sequence at frame rate R from the digital pixel values in the sequence of image frames. The output image frame sequence is representative of the imaged scene and is produced with a latency of no more than approximately 1/R, having a dynamic range of image frame pixel values being represented by a number of digital bits D, where D is less than B. The output image frame sequence can be characterized by a noise-limited resolution of at least a minimum number of line pairs per millimeter as a function of the illuminance of the input light impinging on the pixels of a charged-coupled imaging device.

SUMMARY OF THE DISCLOSED TECHNIQUE

It is an object of the disclosed technique to provide a novel method and system for spatially registering the pixels of an image at a rate faster than the response time of the VOR of humans, which overcomes the disadvantages of the prior art.

In accordance with the disclosed technique, there is thus provided an apparatus for displaying at least one image with respect to a line-of-sight (LOS), with substantially no image latency as perceived by a human user. The LOS is determined between the head of a user and at least one coordinate system established in space, with the coordinate system and the displayed image being in relative motion there between. The apparatus includes an image source, a display processor and a displaying unit. The display processor is coupled with the image source and the displaying unit. The image source provides at least one spatially unregistered image, the display processor spatially registers the spatially unregistered image with the LOS, thereby generating a respective at least one spatially registered image, and the displaying unit displays an at least one spatially registered pixel on a displaying surface. The display processor includes a storage unit, an image processor and a pixel locator. The pixel locator is coupled with the image processor. The storage unit stores the spatially unregistered image, the image processor selects at least one projection pixel to be displayed and the pixel locator determines, in each spatially unregistered image, the location of the spatially registered pixel corresponding to the selected projection pixel.

According to another embodiment of the disclosed technique, there is thus provided a method for displaying at least one image with respect to a line-of-sight (LOS), with substantially no image latency as perceived by a human user. The LOS is determined between the head of a user and at least one coordinate system established in space, with the coordinate system and the displayed image being in relative motion there between. The method includes the procedures of providing at least one spatially unregistered image from an image source, storing the spatially unregistered image, selecting at least one projection pixel to be displayed, spatially registering the spatially unregistered image with the LOS, and displaying an at least one spatially registered pixel. The procedure of spatially registering includes generating a respective at least one spatially registered image, by determining, in each spatially unregistered image, the location of the spatially registered pixel corresponding to the selected projection pixel.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1A:
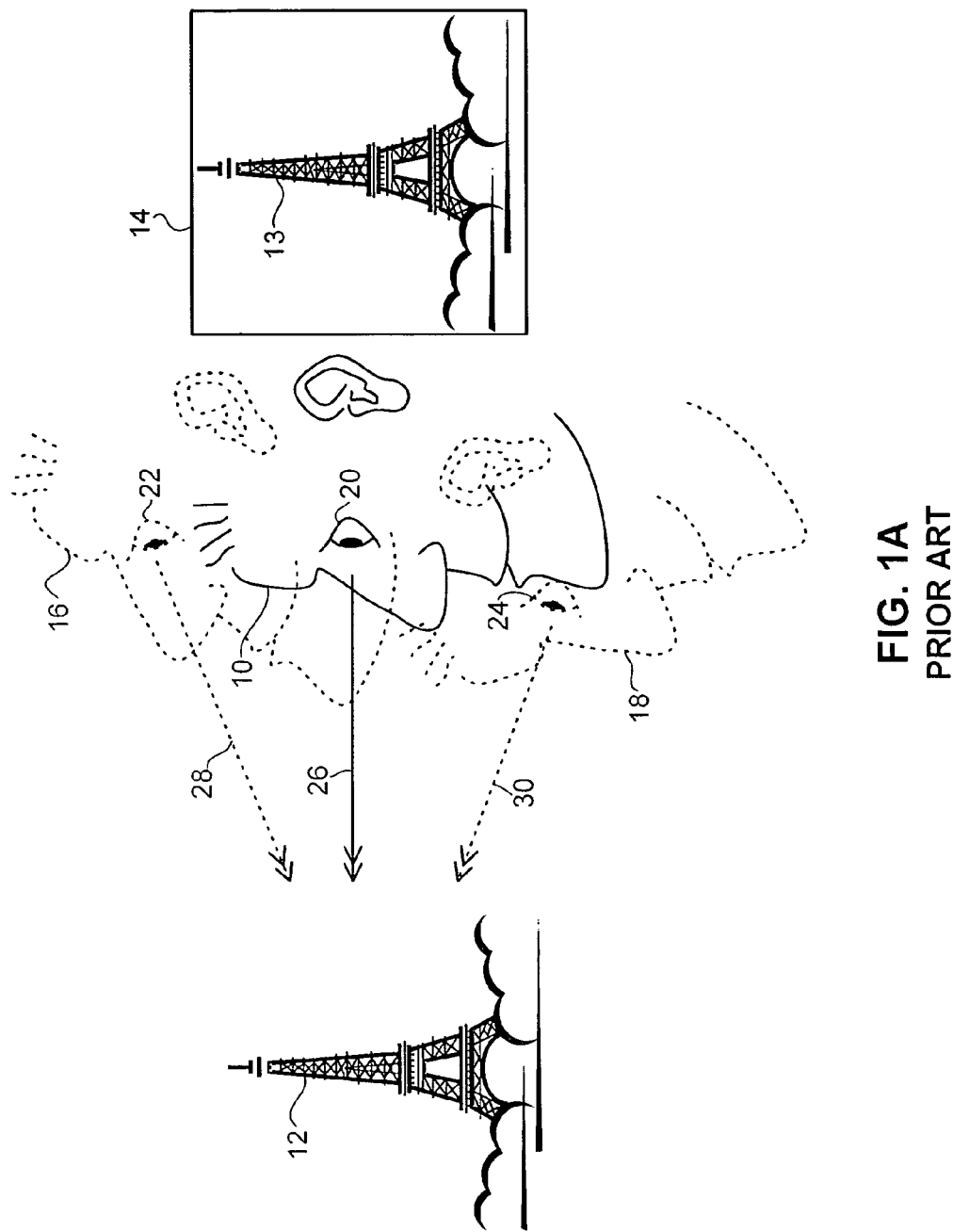
FIG. 1A is an illustration of the vestibulo-ocular reflex, as is known is the art.

The disclosed technique overcomes the disadvantages of the prior art by providing a novel method and system for spatially registering the pixels of an image at a rate faster than the response time of the VOR of humans. In this respect, the latency in spatially registering the image, as perceived by a human user (e.g., a pilot), is minimized. According to the disclosed technique, image pixels to be presented to a pilot are processed, spatially registered and scanned to the HMD of the pilot in real-time. Once the raw images, received from, provided by, or generated by, a camera and from other data sources, are stored in memory, the first image pixel can be spatially registered and projected to a user at a fixed position in less than 1 millisecond. Accordingly, as the amount of time required to spatially register the pixels of an image to be projected to an operator is reduced (i.e., the image latency is reduced), the chance of motion sickness in the operator is also reduced. Also, according to the disclosed technique, once the raw images are stored in memory, no other images need to be stored in memory during the process of spatially registering the pixels of the image to be projected to the operator. It is noted that this is in contrast to the prior art, where each time an image, whether it be the camera image, the symbology or the digital map, is modified (e.g., cropped, rotated, distortion-corrected and the like), the modified image is stored in memory. It is also noted that the disclosed technique is described herein, by way of example, with reference to a pilot in an aircraft cockpit wearing a helmet with an integrated HMD. As such, the disclosed technique can also be used in airplanes, helicopters, land vehicles, sea vehicles, video game systems, heads-up displays and heads-down displays. In general, image latency is a measure of the amount of time it takes to project a spatially registered pixel to a displaying surface once the location of the spatially registered pixel has been found.

It is further noted that the disclosed technique can be used to implement a virtual HUD (herein abbreviated VHUD). A VHUD is an HMD which is used as a replacement for a HUD. VHUDs provide major cost, as well as operational, benefits, which can include: an increase in instrument panel space, a reduction in electronics and weight once needed for a traditional HUD in the cockpit, an improved field of view over a traditional HUD and an enlarged motion box in which the HUD can be seen. By implementing the functionality of an HMD and a HUD into a single system, the display format of images to an operator can be improved, and the situational awareness of the operator can be improved since less time will be required to switch from looking at the HMD to the HUD.

It is also noted that the disclosed technique can be used to implement a virtual multi-function display (herein abbreviated VMFD). A VMFD enables a virtual image of a multi-function display of an aircraft to be presented to the pilot. Multi-function displays can present various types of information to the pilot, for example, weather maps, instrument panel gauges and moving map (real-time tracking) displays. The VMFD can be presented to the pilot such that when he looks to the lower half of the aircraft cockpit, he sees a virtual display. The VMFD can be produced in numerous ways, for example, as a picture of the actual multi-function display of the aircraft, as an image generated according to data received from the aircraft, or both.

In general, as explained in the background of the disclosed technique section, as a pilot moves his head, his VOR corrects his LOS such that his eyes stay aligned on an object he perceives. According to the disclosed technique, the LOS of the pilot is established between the head of the pilot and at least one coordinate system established in space. The coordinate system can be established in real space, thereby giving coordinates to real objects seen outside the cockpit of an aircraft. The coordinate system can also be established in virtual space, thereby giving coordinates to virtual objects projected to a visor of a helmet worn by the pilot.

Figure 4:
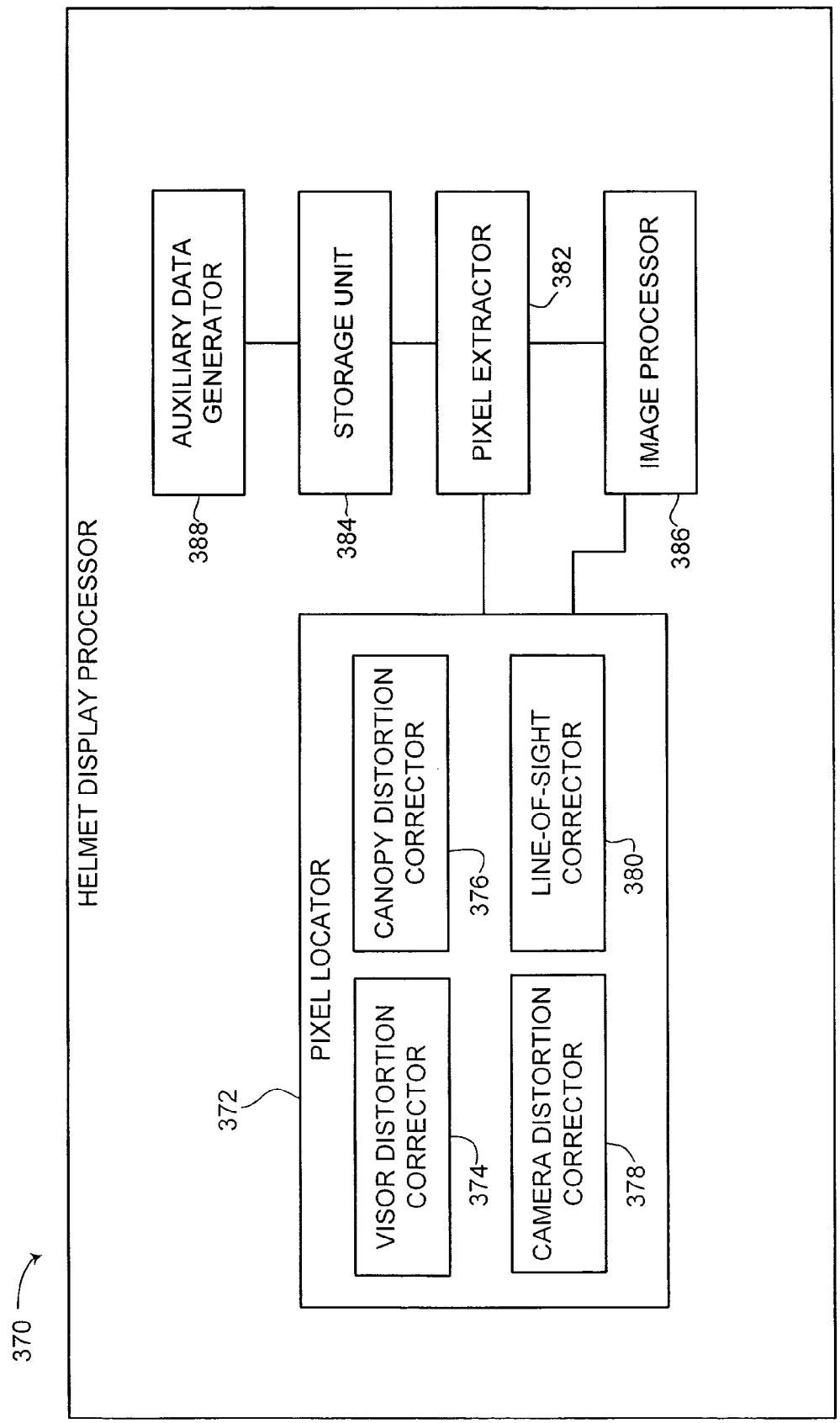
FIG. 4 is a schematic illustration of a helmet display processor, constructed and operative in accordance with an embodiment of the disclosed technique.

Reference is now made to FIG. 4, which is a schematic illustration of a helmet display processor, for displaying images on the visor of a helmet, generally referenced 370, constructed and operative in accordance with an embodiment of the disclosed technique. Helmet display processor (herein abbreviated HDP) 370 includes a pixel locator 372, a pixel extractor 382, a storage unit 384, an image processor 386 and an auxiliary data generator 388. Pixel locator 372 is coupled with pixel extractor 382 and with image processor 386. Pixel extractor 382 is coupled with storage unit 384 and image processor 386. Auxiliary data generator 388 is coupled with storage unit 384. Pixel locator 372 includes a visor distortion corrector 374, a canopy distortion corrector 376, a camera distortion corrector 378 and a LOS corrector 380. Visor distortion corrector 374, canopy distortion corrector 376, camera distortion corrector 378 and LOS corrector 380 are each coupled with one another (not shown). It is noted that HDP 370 is further coupled with a head sensor (not shown), a camera (not shown), an aircraft data system (not shown) and a projection unit (not shown). HDP 370 is integrated into an airborne imaging and vision system. It is noted that the projection unit can be any unit enabled to display or produce an image to a user.

Figure 1B:
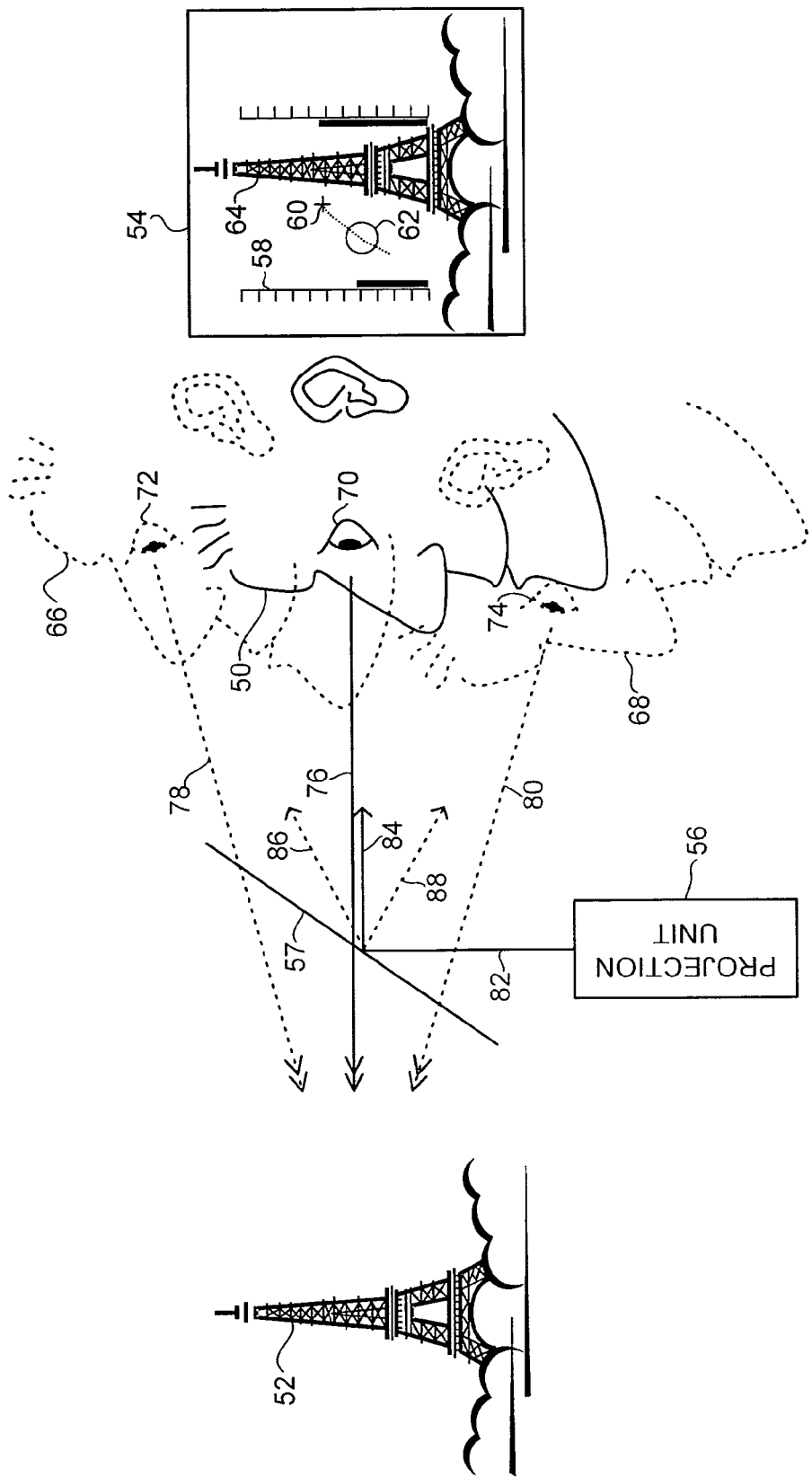
FIG. 1B is another illustration of the vestibulo-ocular reflex, as is known in the art.
Figure 1C:
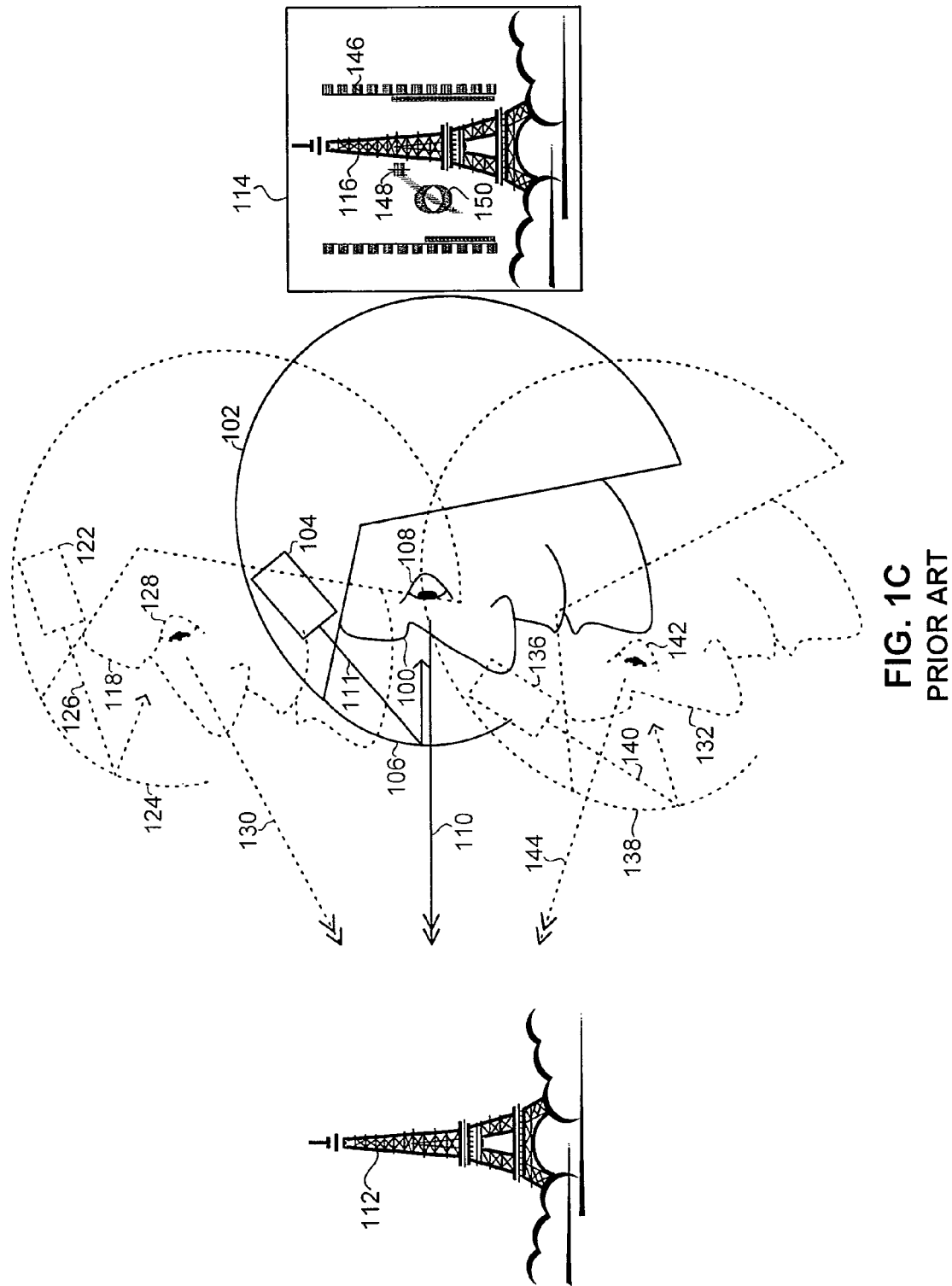
FIG. 1C is a further illustration of the vestibulo-ocular reflex, as is known in the art.
Figure 1D:
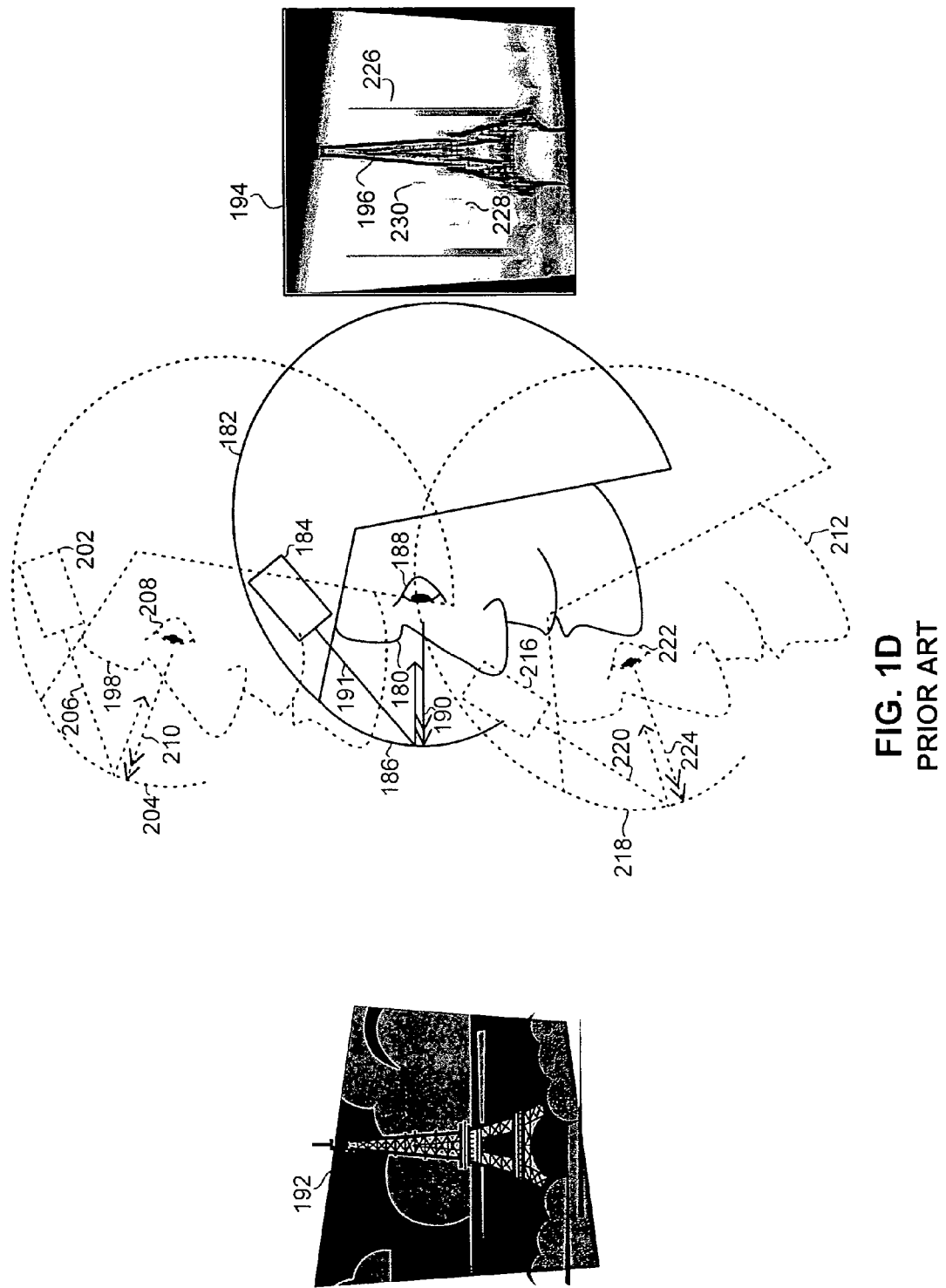
FIG. 1D is another illustration of the vestibulo-ocular reflex, as is known in the art.
Figure 2:
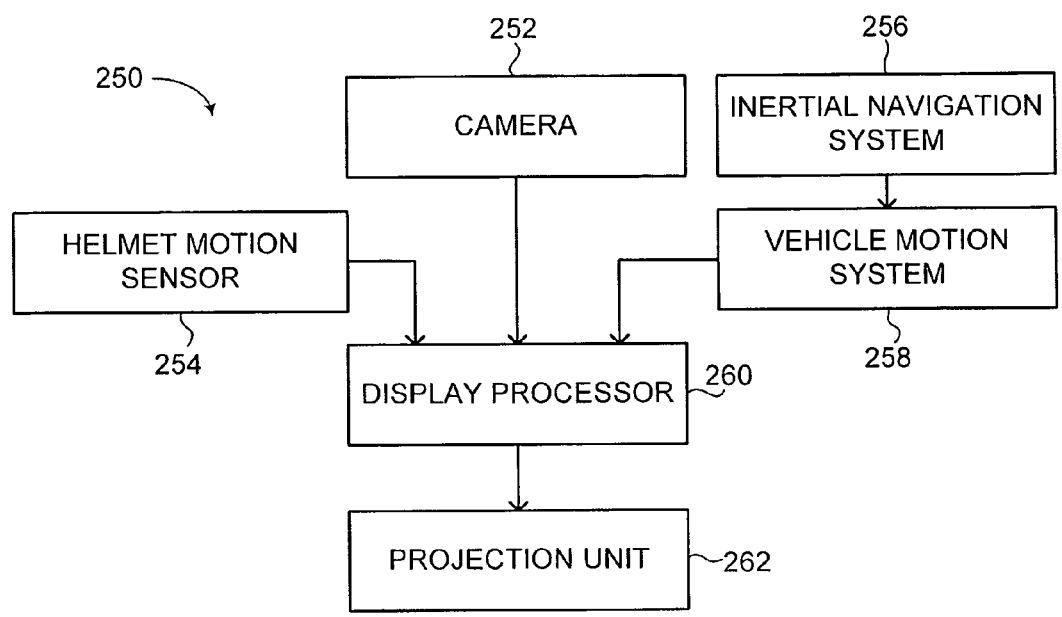
FIG. 2 is a schematic illustration of a prior art airborne vision and imaging system.

The camera may be, for example, an IR camera, a visible light camera, an ICCD camera, an image intensified camera, a sensor fused camera, an aircraft panoramic night vision system and the like. The camera can also be replaced by an image generator which can generate virtual reality images and virtual world images. The image received by, or provided by the camera may be light intensified, or otherwise not normally visible to the human eye. The head sensor is located on the helmet of the pilot (not shown) and measures the movement (i.e., azimuth, elevation, rotation, location in the reference frame of the aircraft, velocity and acceleration) of the head of the pilot in all directions. The head sensor also determines the location and orientation (i.e., the position) of the head of the pilot in relation to the location and orientation of the aircraft. The data determined by the head sensor, is optionally saved in storage unit 384. As explained further below, the data determined by the head sensor is scheduled to be provided to HDP 370 during the time when HDP 370 requires the head sensor data to determine corrected raw pixel locations. The aircraft data system is located on the aircraft (not shown), and measures the movement of the aircraft in all directions (i.e., location and orientation), monitors the position of the aircraft, the movement of the aircraft in all directions, as well as other systems related to the aircraft (i.e., aviation systems), such as a weapons system, a fuel system and the like. The data determined and measured by the aircraft data system is optionally saved in storage unit 384. The aircraft data system can include, for example, an INS, a global positioning system (herein abbreviated GPS) and the like. The projection unit is located on the helmet of the pilot, and projects an image received from, or provided by, the camera, or generated by the image generator, and any other data provided by the aircraft data system, onto the visor of the helmet. As explained above, in reference to FIG. 1D, since the projected image, as perceived by the pilot, moves in relation to at least one of the established coordinate systems in space, the projected image should be spatially registered such that the pilot does not perceive any relative motion between the projected image and at least one of the established coordinate systems in space. According to the disclosed technique, the projected image is spatially registered at a rate fast enough that a human pilot does not perceive noticeable relative motion between the projected image and at least one of the established coordinate systems in space, even though such relative motion does in fact occur.

The camera receives, or provides, an image of an outside scene, or an image of an outside scene is generated, or provided, by the image generator. Objects in the image of an outside scene are positioned in a coordinate system established in real space, whereas objects in an image generated by an image generator are positioned in a coordinate system established in virtual space. The image may be an IR image, a FLIR image, an ICCD image, a night vision image, or it may be light intensified. The camera provides the image to HDP 370. HDP 370 stores the raw camera image in storage unit 384. The head sensor continuously measures the movement of the head of the pilot and provides these measurements to HDP 370, which optionally stores the measurements in storage unit 384. As mentioned above, the head sensor provides head sensor data to HDP 370 is a scheduled manner such that HDP 370 receives the head sensor data as it is required to determine corrected raw pixel locations. The aircraft data system continuously measures and optionally stores the movement of the aircraft and provides these measurements to HDP 370, which optionally stores them in storage unit 384. HDP 370 provides the measurements of the movement of the head of the pilot and the measurements of the movement of the aircraft to pixel locator 372. The aircraft data system can also provide HDP 370 with other data regarding the aircraft, which is optionally stored in storage unit 384, for example, the altitude of the aircraft, the LOS of the weapons system, the amount of fuel left in the aircraft, and the like. Auxiliary data generator 388 can then access this other data from storage unit 384 or from the aircraft data system directly.

Figure 3A:
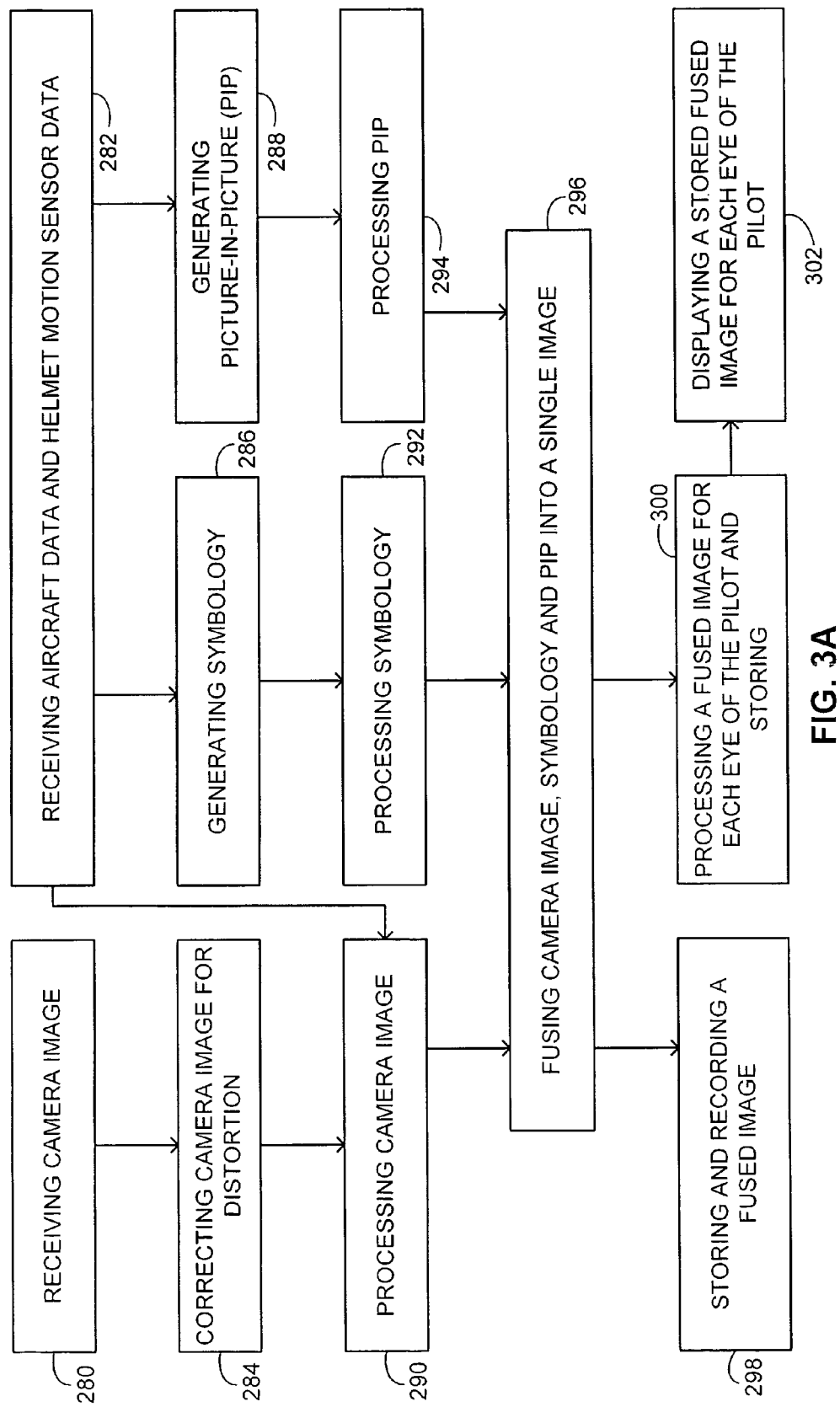
FIG. 3A is a schematic illustration of a prior art method for spatial registration.
Figure 3B:
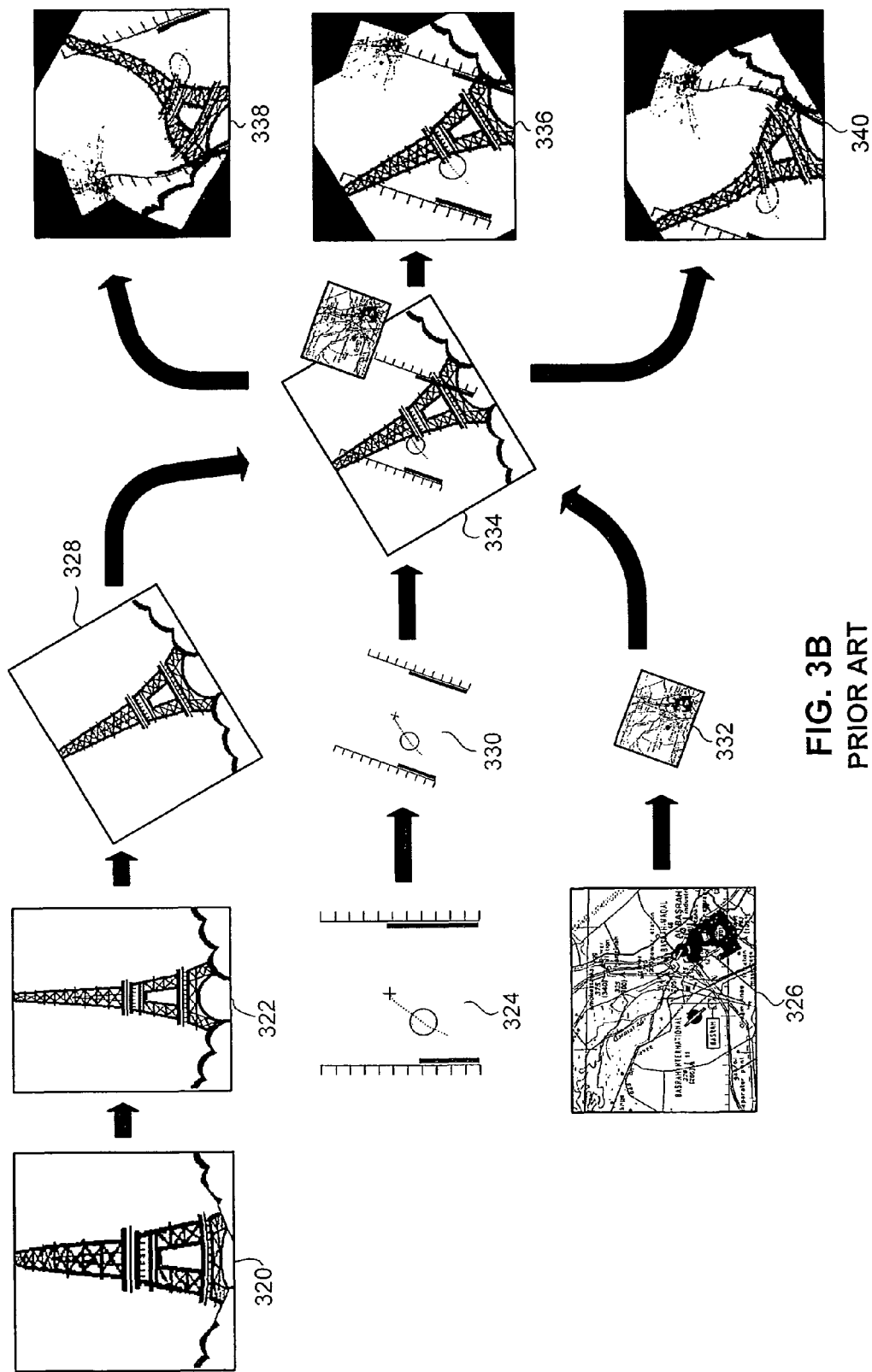
FIG. 3B is a graphical representation of the method of FIG. 3A.

As the raw camera image is being stored in storage unit 384, auxiliary data generator 388 produces a representation of the data received from the aircraft data system. The representation of the data can be, for example, in the form of static as well as dynamic symbology. Data from the aircraft data system can also be used to generate symbology which is not a direct representation of the data. Static symbology can include, for example, vehicle altitude, vehicle velocity, adding scale, the horizon and the aiming course, with each representation of the data being saved as a separate image in storage unit 384. Static symbology is always projected to the same location on the visor of the helmet. It is therefore enslaved to the LOS of the pilot and moves in the reference frame of the aircraft as the pilot turns his head. Static symbology can also be projected to the pilot via a VHUD, a VMFD or both, although in general, all the symbology projected to a pilot via a VHUD is dynamic. Dynamic symbology can include crosshairs and target markers (see, for example, with reference to FIG. 1B, crosshair 60, target marker 62 and level indicator 58), with each representation of the data being saved as a separate image in storage unit 384. Dynamic symbology is stabilized in the external reference frame such that the pilot always sees the symbology at a fixed location in the external reference frame. Dynamic symbology is therefore not projected to a fixed location on the visor of the helmet, but "moves" across the visor of the helmet such that irregardless of the orientation of the head of the pilot, the symbology will be seen at the same location in the external reference frame. The representation of the data can also be, for example, in the form of a digital map (see, with reference to FIG. 3B, image 326), which may be placed in the final image, projected to the pilot, in a PIP format. The representation of the data can also be data from a weapons camera, a target zoom camera, and the like. The produced and generated symbology and the digital map are stored in storage unit 384. It is noted that storing the images can take about 16.6 milliseconds (i.e., usually the same rate as the projection unit update rate). Once the raw camera image, as well as the symbology and the digital map (herein referred to as the raw images) are stored in memory, image processor 386 begins processing and simultaneously scanning the raw images to be projected to the pilot as an updated image of the outside scene. The raw images can also include a weapons view image, an HMD day camera image, an HMD night camera image, a three-dimensional video input and internal calibration patterns. In general, the defining characteristic of the raw images is that they have not been spatially registered (i.e., they are spatially unregistered) when they are initially stored in memory (although some of them may have been processed in a certain manner before being initially stored in memory). It is noted that the list of raw images in the disclosed technique is not limited to three sources (i.e., raw camera image, symbology and digital map), but can include a plurality of sources. For example, according to the disclosed technique, N video images and M symbology images can be supported in the processing. The processing is done to "superimpose" the raw images over one another, correct the distortion in the raw images and to ensure that the pixels projected to the pilot are correctly spatially registered in accordance with a fixed position relative to the pilot. It is noted that according to the disclosed technique, the raw images are not traditionally superimposed, and then subsequently stored in storage unit 384. Rather, the image seen by the pilot is perceived by him as a superposition of the raw images, as described further below. The processing can also include generating a three-dimensional image of the image to be projected to the pilot from a processed two-dimensional image.

Following the scanning pattern of the projection unit (for example, raster scanning, stroke scanning and the like), image processor 386 selects the location of the pixel which is to be projected to the visor of the pilot. The location of this pixel can be designated as (x,y). It is noted that in another embodiment of the disclosed technique, image processor 386 selects the locations of a plurality of pixels to be projected to the visor of the pilot. Pixel locator 372 then determines the location of the pixels from the raw images, already stored in memory, that will be "superimposed" to form pixel (x,y). Pixel extractor 382 then extracts (i.e., reads) the corresponding pixels from the stored raw images in storage unit 384 and provides them to image processor 386. It is noted that pixel extractor 382 is an optional element, and that image processor 386 can read (i.e., retrieve) the corresponding pixels, from the stored raw images in storage unit 384, directly. Image processor 386 then manipulates the grey levels (e.g., transparency, contrast, brightness, gamma correction, filtering, layer level and image preference) of the corresponding pixels. It is noted that image processor 386 can also manipulate the luminance levels and the chrominance levels (e.g., transparency, contrast, brightness, gamma correction, filtering, layer level and image preference in a color image) of the corresponding pixels. Since the manipulation of the grey levels of the corresponding pixels includes determining the layer levels of those pixels, after the grey levels of those pixels have been manipulated, the corresponding pixels have been "superimposed," as mentioned above, because their layer levels have been determined. Data from the aircraft data system may be used by image processor 386 to manipulate the grey levels, the luminance levels, the chrominance levels, or a combination thereof, of the corresponding pixels. The corresponding pixel with the highest layer level is then projected to the visor of the pilot at the location of (x,y). Therefore, effectively, the corresponding pixels have been "superimposed." In this respect, as HDP 370 receives data from the aircraft data system and the head sensor needed to determine the location of the corresponding pixels, HDP 370 synchronizes this data with projecting the highest layer level manipulated pixel to the visor of the pilot. In real-time, as HDP 370 receives data from the aircraft data system and the head sensor, image processor 386 determines corrected raw pixel locations, extracts raw pixels from storage unit 384 and manipulates them, while the projection unit projects the highest layer level manipulated pixel to the visor of the pilot with minimal image latency. As mentioned above, HDP 370 is synchronized to be provided with head sensor data as HDP 370 needs the head sensor data to determine corrected raw pixel locations. Due to this synchronization, the most up-to-date head sensor data is used by image processor 386 to determine the corrected raw pixel locations. In a further embodiment of the disclosed technique, the manipulated raw image pixel is provided to a recording unit (not shown), which records and stores the pixel. It is noted that this recorded and stored pixel has not undergone distortion correction for being projected onto a curved surface, like a visor or a canopy. The next pixel to be projected to the visor of the pilot following the scanning pattern of the projection unit, for example, the pixel located at (x+1, y), is then selected. The corresponding pixels in the stored raw images are then determined, extracted and manipulated before being projected (i.e., before projecting the manipulated pixel with the highest layer level) to the visor of the pilot at the location of (x+1, y).

Some of the components of pixel locator 372 correct for distortion inherent in the raw images. Other components crop, shift, scale, rotate and perform image correction of the raw images according to the direction of the head of the pilot. Pixel locator 372 determines the corresponding corrected locations of pixels in the raw images that will be "superimposed" to form the spatially registered, optically corrected and LOS-corrected-pixel (x,y) in the image projected to the pilot. The corrections are done using known data, as explained below, and using data that is continuously available, updated and provided in a scheduled manner to HDP 370, for example, head sensor data.

Pixels are the smallest elements that make up a digital image, and are therefore either drawn on a display or not drawn on the display (i.e., a pixel has no fuzzy state of being partially drawn and partially not drawn simultaneously). Therefore, when a digital image is corrected, for example, for optical distortion, the correction involves determining which pixels from the raw image are to be drawn, and where, and which are not. For example, with reference to FIG. 3B, when raw image 320 is corrected for optical distortion to produce image 322, the correction involves determining which pixels in 320 will be written, and where, in image 322, and which will not.

Visor distortion corrector 374 corrects for distortion inherent in the curved surface of the visor, such that projected pixel (x,y) will be properly seen on the visor of the pilot. The correction involves determining the location of a pixel (x', y') in the raw images such that when (x',y') is scanned in the projected image to the pilot in the position of (x,y), the pixels forming the projected image will appear undistorted. In another embodiment of the disclosed technique, this correction involves determining the location of two pixels, ($x'_{right}$, $y'_{right}$) and ($X'_{left}$, $Y'_{left}$), one for each eye of the pilot, in the raw images, such that when ($x'_{right}$,$y'_{right}$) and ($x'_{left}$, $y'_{left}$) are scanned respectively in the projected image to the respective eye of the pilot in the position of (x,y), the pixels forming the projected image will appear undistorted. Visor distortion corrector 374 uses the following equation to determine the location of pixel (x',y')

$$(x',y') = \text{Visor\_DC}(x,y) \quad (1)$$

where (x,y) is the location of the pixel to be projected to the pilot, Visor_DC is a function which corrects for the distortion in the visor and (x', y') is the location in the raw images where the pixels used to fill location (x,y) in the projected image to the pilot should be taken from. Visor_DC can be a known polynomial which accounts for the distortion in the visor, a look-up table (herein abbreviated LUT), or other functions which allow the corrected location of pixel (x,y) to be determined, as is known in the art. Visor_DC is known data, which is stored in visor distortion corrector 374.

Once the visor-distortion-corrected-pixel-location (x',y') has been determined, canopy distortion corrector 376 uses (x',y') to correct the distortion inherent in the canopy of the aircraft. The distortion of the canopy is corrected for if the camera is located inside the cockpit, or if information is to be projected to the pilot on the canopy. The correction involves determining the location of a pixel (x", y") in the raw images, based on the corrected-visor-pixel-location (x',y') such that when (x",y") is scanned in the projected image to the pilot in the position of (x,y), the pixels forming the projected image will appear undistorted having taken into account the distortion of the visor and the canopy as well. Canopy distortion corrector 376 uses the following equation to determine the location of pixel (x",y")

$$(x'',y'') = \text{Canopy\_DC}(x',y',El,Az,Ro) \quad (2)$$

where (x',y') is the location of the pixels in the raw images to be projected to the pilot after correction for the distortion in the visor has been executed, Canopy_DC is a function which corrects for the distortion in the canopy of the aircraft and takes into account the elevation (El), azimuth (Az) and rotation (Ro) of the helmet of the pilot, and (x",y") is the location in the raw images where the pixels used to fill location (x,y) in the projected image to the pilot should be taken from. Canopy_DC can be a known polynomial which accounts for the distortion in the canopy, a LUT, or other functions which allow the corrected location of pixel (x,y) to be determined, as is known in the art. Canopy_DC is known data which is stored in canopy distortion corrector 376.

Once the canopy-distortion-corrected-pixel-location (x", y") has been determined, camera distortion corrector 378 uses (x",y") to correct for any distortion (for example, pincushion distortion or barrel distortion) in the raw camera image. If the image was not recorded by the camera but was generated by the image generator, then no distortion needs to be executed on the image. The correction involves determining the location of a pixel (x''', y''') in the raw images, based on the corrected-canopy-pixel-location (x",y") such that when (x''', y''') is scanned in the projected image to the pilot in the position of (x,y), the pixels forming the projected image will appear undistorted having taken into account the distortion of the visor, the canopy and the camera. Camera distortion corrector 378 uses the following equation to determine the location of pixel (x''',y''')

$$(x''',y''') = \text{Camera\_DC}(x'',y'') \quad (3)$$

where (x",y") is the location of the pixels in the raw images to be projected to the pilot after correction for the distortion in the canopy has been executed, Camera_DC is a function which corrects for the distortion in the camera, and (x''',y''') is the location in the raw images where the pixels used to fill location (x,y) in the projected image to the pilot should be taken from. Camera_DC can be a known polynomial which accounts for the distortion in the camera, a LUT, or other functions which allow the corrected location of pixel (x,y) to be determined, as is known in the art. Camera_DC is known data which is stored in camera distortion corrector 378.

Once the camera-distortion-corrected-pixel-location (x''', y''') has been determined, LOS corrector 380 uses (x''',y''') to spatially register the image to be projected to the pilot at a fixed position in accordance with the measurements of the movement of the head of the pilot. The spatial registration involves determining the location of a pixel (x'''', y'''') in the raw images, based on the corrected-camera-pixel-location (x''',y''') such that when (x'''',y'''') is scanned in the projected image to the pilot in the position of (x,y), the pixels forming the projected image will be spatially registered at a fixed position, having taken into account the distortion of the visor, the canopy and the camera. Spatial registration may involve operations that can include, for example, scaling, cropping, shifting, rotating, Euler corrections, polynomial approximations and spatial filtering of the raw images. LOS corrector 380 uses the following equations to determine the location of pixel (x'''',y'''')

$$x'''' = Kx[\cos(\alpha) - \sin(\alpha)]x''' + \text{Shift}(x''') \quad (4)$$

$$y'''' = Ky[\cos(\alpha) - \sin(\alpha)]y''' + \text{Shift}(y''') \quad (5)$$

where (x''',y''') is the location of the pixels in the raw images to be projected to the pilot after correction for the distortion in the camera has been executed, Kx and Ky are scaling factors, α is a rotation value, and (x'''',y'''') is the location in the raw images where the pixels used to fill location (x,y) in the projected image to the pilot should be taken from. Kx, Ky and α are known data which are stored in LOS corrector 380.

Equations (4) and (5) are examples of the types of equations that can be used to determine (x"",y""). Other equations can be used that factor in a scaling factor, cropping parameters, an Euler correction, polynomial approximations, predictions of the position of the head of the pilot, which can be predicted by known head movement prediction algorithms, and the like. An Euler correction involves a multiplication by an Euler rotation matrix in order to transform corrections on the location of pixels in the LOS of the pilot from Cartesian coordinates to polar coordinates.

It is noted that each of the above corrections are executed for each raw image. Therefore, the corrected pixel location $(x"",y"")_A$ determined for raw image A may not be the same location as the corrected pixel location $(x"",y"")_B$ determined for raw image B. It is also noted that the corrections described above are not executed on the entire image of the raw images. The corrections are done at the level of a pixel, and yield only an address in memory as to which pixels should be selected from the raw images to be "superimposed" to form the pixel to be projected to the pilot following the scanning pattern of the projection unit. It is noted that none of these corrections actually involve correcting the raw images and storing the corrected raw images in memory. All these corrections only involve determining the location of the pixels to be selected from the raw images such that the projected pixel to the pilot will be corrected for various distortions and changes in the LOS of the pilot. It is also noted that the determined-corrected-location (x"",y"") may be different for each raw image. It is further noted that the order of corrections executed is not restricted to the order in which they have been presented. For example, corrections regarding the LOS of the pilot could be executed first, followed by corrections for the distortion of the canopy, then the camera and finally the visor. It is also noted that the disclosed technique is not limited to the four corrections enumerated above, but can include other known corrections, operations and functions to raw images. It is further noted that the corrections used to find corrected pixel locations (i.e., LOS corrections, canopy corrections, camera corrections, visor corrections and the like) can be unified into a single correction. For example, Equations (1), (2), (3), (4) and (5) can be simplified into a single correction equation. With a single correction equation, pixel locator 372 can determine corrected pixel locations without the need of additional hardware components. Therefore, visor distortion corrector 374, canopy distortion corrector 376, camera distortion corrector 378 and LOS corrector 380 can be replaced by a single image corrector (not shown). It is also noted that other known data relating to the aircraft, the pilot or both, which pixel locator 372 may require to determine the corrected location of pixel (x,y), can be stored in storage unit 384.

As mentioned above, once the corrected location of pixel (x,y) is determined, for example pixel (x"",y""), by pixel locator 372 in the raw images, pixel extractor 382 extracts the pixels positioned at (x"",y"") from the raw images, which are stored in storage unit 384. The position (x"",y"") may be different for each of the raw images. In another embodiment of the disclosed technique, once the corrected location of pixel (x,y) is determined, for example pixel (x"",y""), in the raw images, pixel extractor 382 extracts the pixels in the raw images positioned at (x"",y"") and other neighboring pixels from each raw image. For example, three neighboring pixels may be selected. The neighboring pixels can be selected from the following positions relative to the correct location of pixel (x,y): to the right, to the left, above, below, diagonally to the right above, diagonally to the right below, diagonally to the left above and diagonally to the left below.

Pixel extractor provides these extracted pixels to image processor 386. Image processor 386 manipulates the grey levels, the luminance levels, the chrominance levels, or a combination thereof, of each extracted pixel separately according to the data received from the aircraft data system, which includes "superimposing" them. The manipulation of grey levels, luminance levels, chrominance levels, or a combination thereof, can include α-β filtering, as well as algorithms that utilize antialiasing. In the embodiment of the disclosed technique where neighboring pixels are extracted besides the pixels located at (x"",y"") in each raw image, image processor 386 filters, for each raw image, the pixel located at (x"",y"") as well as its neighboring pixels by a bilinear interpolation. Image processor 386 can also filter, for each raw image, the pixel located at (x"",y"") as well as its neighboring pixels by antialiasing. The bilinear interpolation determines interpolated grey levels, luminance levels, chrominance levels, or a combination thereof, for the extracted pixel (x"",y"") and its neighboring pixels. It is noted that in prior art systems, bilinear interpolations are executed by using a convolution of typically 3 by 3 or 4 by 4 pixels over an entire image. When three neighboring pixels are selected, the bilinear interpolation can be executed using the following expression $$\text{Grey\_level}(x"",y"")=A(1-\Delta x)(1-\Delta y)+B(\Delta x)(1-\Delta y)+C(1-\Delta x)(\Delta y)+D(\Delta x)(\Delta y) \quad (6)$$

where Grey_level(x"",y"") is the interpolated grey levels for the pixel in the raw images located at position (x"",y""), A is the current grey level of the pixel located in the raw images at position (x"",y""), B, C and D are the grey levels of the three neighbor pixels of (x"",y"") in the raw images, and Δx and Δy are subpixel information for the pixel in the raw images located at (x"",y""). It is noted that a modified version of Equation (6) can be used when the bilinear interpolation is executed on the luminance levels, the chrominance levels, or a combination thereof. After the bilinear interpolation has been executed on all the extracted pixels from all the raw images, the extracted pixel with the highest layer level, with interpolated grey levels, is projected to the visor of the pilot. It is noted that the bilinear interpolation can be executed using N neighboring pixels.

It is noted that in order to provide a stable final "superimposed" image projected to the pilot with minimal smearing, vibrations and jitter, it is required that the manipulated raw image pixels be updated at the maximum refresh rate of the projection unit. If the projection unit is a flat panel display (herein abbreviated FPD), the maximum refresh rate may be 120 Hz or higher. In general, the refresh rate for the projection unit must not be below 60 Hz, although the update rate for the generated auxiliary data may be lower. Also, in order to overcome the VOR (i.e., to project stabilized, spatially corrected images to the pilot at a rate faster than the VOR), it is recommended that the overall refresh rate of HDP 370 should be at least 60 Hz.

As mentioned above, the manipulated pixel with the highest layer level is projected to the visor of the pilot at the location of (x,y). The next pixel to be projected to the visor of the pilot following the scanning pattern of the projection unit, for example, the pixel located at (x+1, y), is then selected. The corresponding pixels in the stored raw images are then determined, extracted and manipulated (which includes "superposition" of the corresponding pixels) before being projected to the visor of the pilot at the location of (x+1, y).

Image processor 386 continuously selects the location of pixels which are to be projected to the visor of the pilot. Once all the pixels forming a complete image have been selected, their corresponding locations in the raw images determined, have been extracted, manipulated and projected to the visor of the pilot, another raw camera image is received, or generated, from the camera or from the image generator, and updated auxiliary data is generated anew in auxiliary data generator 388 and stored in storage unit 384. It is noted that the processing and scanning time for a single pixel is on the order of nanoseconds. As such, the time required to spatially register, optically correct and scan a single pixel to the image projected on the visor of the pilot, once the raw images have been stored in memory, is less than a millisecond. At such rates, the spatial registration and scanning of the first pixel projected to the pilot occurs in real-time. It is noted that using the disclosed technique, the amount of time required to update a projected image to the pilot is 16.6 milliseconds, the time required to provide all the pixels to the visor of the pilot. Furthermore, since the image projected to the pilot at a fixed position is updated at a rate which is comparable to the response time of the VOR, as the pilot moves his head, his VOR will be able to keep his eyes aligned on the image. It is also noted, that according to the disclosed technique, since the time to spatially register an image is decreased, the latency in event registration is therefore reduced. In general, only the head sensor data is required to spatially register the image projected to the pilot. Measurements regarding the motion of the aircraft, or of a vehicle, are needed to properly register events with a minimal amount of latency.

Figure 5A:
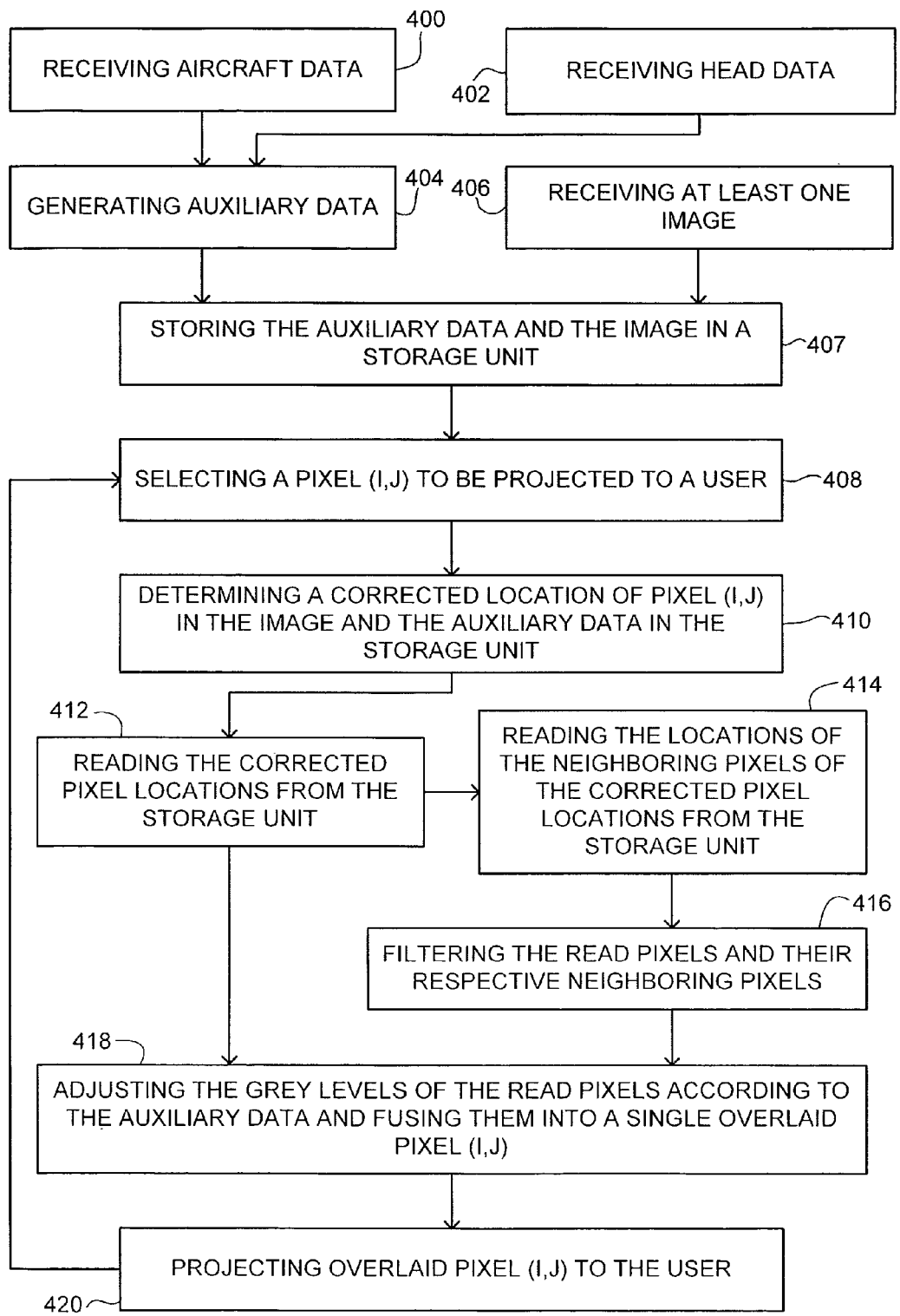
FIG. 5A is a schematic illustration of a method for real-time image scanning and processing, operative in accordance with another embodiment of the disclosed technique.
Figure 5B:
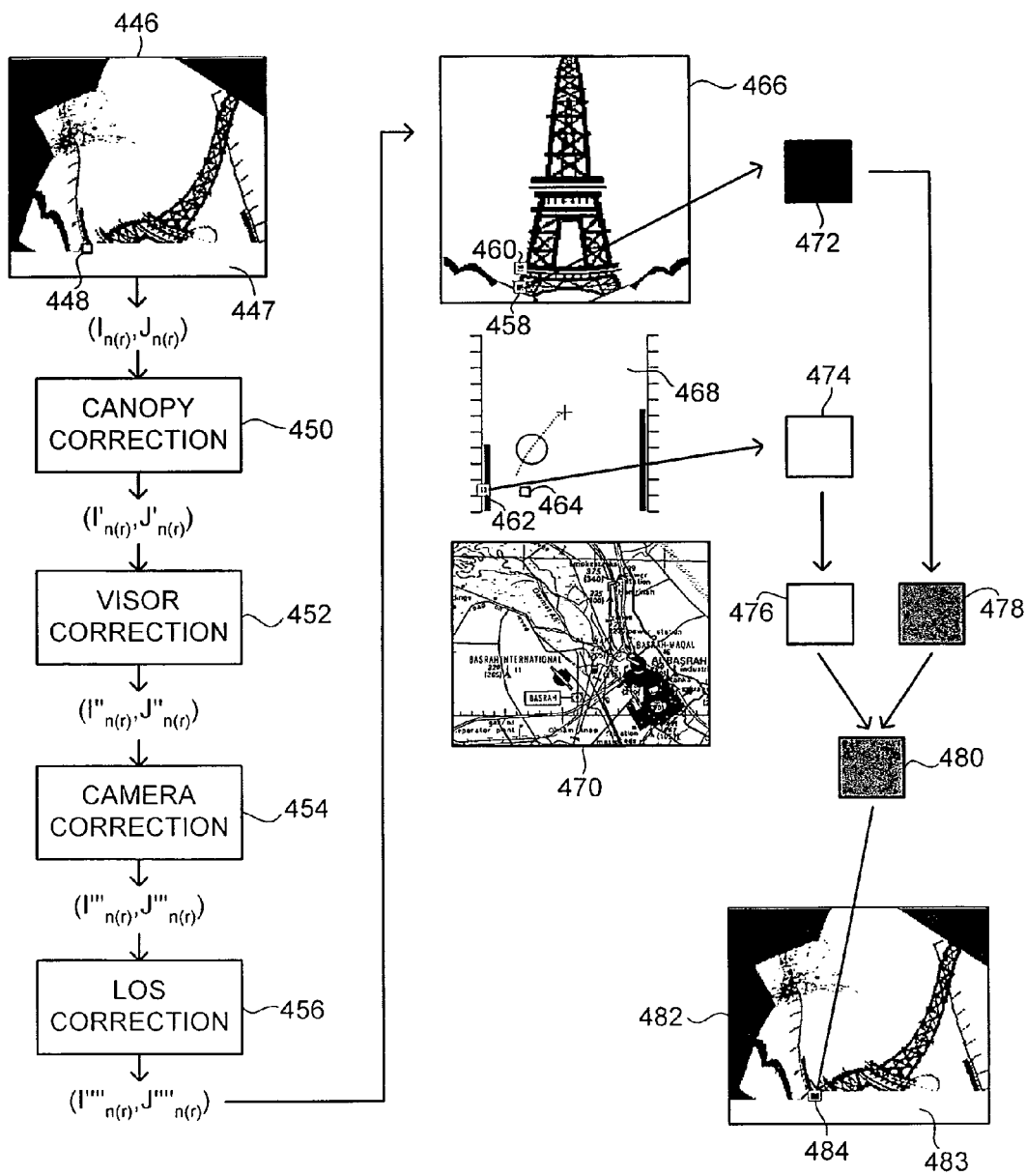
FIG. 5B is a graphical representation of the method of FIG. 5A.

Reference is now made to FIGS. 5A and 5B. FIG. 5A is a schematic illustration of a method for real-time image scanning and processing, operative in accordance with another embodiment of the disclosed technique. FIG. 5B is a graphical representation of the method of FIG. 5A. It is noted that in FIG. 5B, the graphical representation of the method of FIG. 5A is shown for only one image, which is projected to the right eye of a user. In general, according to the disclosed technique, a plurality of images can be generated simultaneously, for example, an image to be projected to the right eye of the user, an image to be projected to the left eye of the user, and an image to be stored in a storage unit. Analogous graphical representations of FIG. 5B for an image to be stored and for an image to be projected to the left eye of the user may be derived from FIG. 5B.

In procedure 400, aircraft data, is received. The aircraft data can include the position of the aircraft, the movement of the aircraft in all directions, as well as other systems related to the aircraft (i.e., aviation systems), such as a weapons system, a fuel system and the like. With reference to FIG. 4, the aircraft data system monitors the position of the aircraft, the movement of the aircraft in all directions, as well as other systems related to the aircraft (i.e., aviation systems), such as a weapons system, a fuel system and the like, and optionally stores this data in storage unit 384.

In procedure 402, data about the head of the pilot is received. Data about the head of the pilot can include measurements of the movement of the head of pilot in all directions and at various angles and rotations, for example, azimuth, elevation, rotation, spatial location, velocity and acceleration. Data about the head of the pilot can also include the location and orientation (i.e., the position) of the head of the pilot in relation to the location and orientation of the aircraft. The data about the head of the pilot is received in a synchronized manner as the data is needed in procedure 410 below to determine corrected pixel locations. With reference to FIG. 4, the head sensor is located on the helmet of the pilot (not shown) and measures the movement (i.e., azimuth, elevation, rotation, location in the reference frame of the aircraft, velocity and acceleration) of the head of the pilot in all directions. The measurements of movement are optionally stored in storage unit 384. It is noted that procedures 400 and 402 can be executed simultaneously.

In procedure 404, auxiliary data, representative of the aircraft data and pilot head data, is generated. The generation of the auxiliary data may require the use of the aircraft data received in procedure 400. The auxiliary data generated can also be presented to the pilot via a VHUD, a VMFD or both. The auxiliary data can include, for example, aircraft symbology (including both static and dynamic symbology), digital maps, data from a weapons camera, a target zoom camera, and the like. The auxiliary data can include M symbology images. With reference to FIG. 5B, an image 468 represents a stored raw image of dynamic symbology generated in procedure 404. An image 470 represents a stored raw image of a digital map generated in procedure 404. With reference to FIG. 4, auxiliary data generator 388 produces a representation of the data received from the aircraft data system. The representation of the data can be, for example, in the form of static as well as dynamic symbology, with each representation of a particular type of data saved as a separate image in storage unit 384. The representation of the data can also be, for example, in the form of a digital map (see, with reference to FIG. 3B, image 326), which may be placed in the final image, projected to the pilot, in a PIP format. The representation of the data can also be data from a weapons camera, a target zoom camera, and the like.

In procedure 406, at least one image is received, or generated. According to the disclosed technique, images from N video sources may be received, or generated, and stored. The image may be, for example, a raw camera image. The image, along with the auxiliary data can be referred to as the raw images. The raw camera image received may be light intensified, a FLIR image, an ICCD image, a night vision image or otherwise not normally visible to the human eye. The raw camera image may also be generated. It is noted that the list of images in the disclosed technique is not limited to three sources (i.e., raw camera image, symbology and digital map), but can include a plurality of sources. It is also noted that the raw camera image may have inherent distortions due to the optics of the camera. If the image is generated, then no distortions will be present therein. With reference to FIG. 5B, an image 466 represents a stored raw camera image. Images 468 and 470 also represent stored raw images. With reference to FIG. 4, the camera receives, or an image generator generates, an image of an outside scene. The camera provides the image to HDP 370. HDP 370 stores the raw camera image in storage unit 384. It is noted that procedure 406 can be executed simultaneously as procedures 400 to 404 are executed.

In procedure 407, the auxiliary data generated in procedure 404 and the at least one image received, or generated, in procedure 406, are stored in a storage unit. With reference to FIG. 4, the camera provides the image to HDP 370. HDP 370 stores the raw camera image in storage unit 384. The data determined by the head sensor is optionally saved in storage unit 384. The data determined and measured by the aircraft data system is optionally saved in storage unit 384.

In procedure 408, following the scanning pattern of a projection unit (for example, raster scanning, stroke scanning and the like), the location of a pixel to be projected to the visor of a user is selected. In an alternative to procedure 408, a plurality of pixels to be projected to the visor of the user are selected. The user may be an aircraft pilot. The location of this pixel can be designated as (x,y). With reference to FIG. 5B, an image 446 represents a final, manipulated image which is being projected to the visor of the pilot. Following the raster scan pattern of image 446, pixel 448 is selected to be projected to the visor of the pilot. Pixel 448 is located at position $(I_{n(r)}, J_{n(r)})$, where the subscript (r) designates that the image is to be projected to the right eye of a user. In image 446, only a portion of the pixels of image 446 have already been updated and projected to the pilot according to the method described with reference to FIG. 5A, therefore a section 447 of image 446 is still not updated. For purposes of clarity, the not updated section 447 of image 446 has been omitted. It is noted that image 446 represents an image projected to the right eye of the pilot. The final manipulated image is a "superposition" of the raw camera image, and the representation of the aircraft data, for example, the static and dynamic symbology and a digital map. The final manipulated image is a processed image in that the pixels that constitute it have been correctly spatially registered in accordance with a fixed position relative to the pilot. With reference to FIG. 4, once the raw camera image, as well as the symbology and the digital map (herein referred to as the raw images) are stored in memory, image processor 386 selects the location of the pixel which is to be projected to the visor of the pilot.

In procedure 410, the location of the pixels from the raw images in the storage unit that will be superimposed to form pixel (I,J) are determined. The raw images may be stored, for example, in memory buffers. Due to distortion inherent in the raw images, and changes in the LOS of the pilot and his head position, corrected locations of pixels in the raw images in the storage unit that will be superimposed to form the spatially registered, optically corrected and LOS-corrected-pixel (I,J) in the image projected to the pilot need to be determined. The determination can include correcting any distortion (for example, pincushion distortion or barrel distortion) in the raw images. The corrections are done using known data, such as aircraft data and head data, which are measured respectively in procedures 400 and 402. As mentioned above, the head data measured in procedure 402 is synchronized to be received when the data is required, in procedure 410, to determine corrected locations of pixels in the raw images. In this respect, the most up-to-date data regarding the head of the pilot is used to determine the corrected locations of pixels in the raw images. The corrections are executed using known polynomials, LUTs, Euler corrections, polynomial approximations and the like, all of which can be used to correct for distortion inherent in the raw images, or the images projected to the visor of the pilot. The corrections can also include scaling, cropping, shifting, rotating, polynomial approximations and spatially filtering in accordance with the measurements of the movement of the head of the pilot such that the spatial location of the image projected to the pilot is corrected in accordance with the LOS of the pilot. The corrections can further include predictions of the position of the head of the pilot, which can be predicted by known head movement prediction algorithms. The corrections are executed to determine the location of pixels to be read (i.e., retrieved) from the storage unit such that they will be spatially registered in the image projected to the pilot. Examples of distortion include canopy distortion, visor distortion and camera distortion. The corrections for the visor distortion and the canopy distortion can refer to determining locations of pixels in the raw images such that the projected image will be properly distorted such that it will be seen properly on the visor of the pilot, on the canopy of the aircraft, or on both. As is known in the art, both the canopy and the visor are curved surfaces, each having an inherent distortion. It is noted that the determination of the location of the pixels from the raw images that will be superimposed to form pixel (I,J) is executed for each raw image.

With reference to FIG. 5B, after pixel $(I_{n(r)}, J_{n(r)})$ has been selected from image 446, a canopy correction 450 using Equation (2) is executed on that pixel location. After the canopy correction, a new, corrected location for the pixel is determined, which is $(I'_{n(r)}, J'_{n(r)})$. Similarly, after canopy correction 450 has been executed, a visor correction 452 using Equation (1) is executed on pixel location $(I'_{n(r)}, J'_{n(r)})$. After the visor correction, a new, corrected location for the pixel is determined, which is $(I''_{n(r)}, J''_{n(r)})$. After visor correction 452 has been executed, a camera correction 454 using Equation (3) is executed on pixel location $(I''_{n(r)}, J''_{n(r)})$. After the camera correction, a new, corrected location for the pixel is determined, which is $(I'''_{n(r)}, J'''_{n(r)})$. After camera correction 454 has been executed, a LOS correction 456 using Equations (4) and (5) is executed on pixel location $(I'''_{n(r)}, J'''_{n(r)})$. LOS correction 456 can also include an Euler correction on pixel location $(I'''_{n(r)}, J'''_{n(r)})$. After the LOS correction, a new, corrected location for the pixel is determined, which is $(I''''_{n(r)}, J''''_{n(r)})$. It is noted that the corrections executed on pixel $(I_{n(r)}, J_{n(r)})$ are done for each raw image. It is also noted that canopy correction 450, visor correction 452, camera correction 454 and LOS correction 456 can be unified into a single correction which yields $(I''''_{n(r)}, J''''_{n(r)})$ (the corrected location for a given pixel) directly. It is further noted that the order of the corrections can be altered. For example, camera correction 454 can be executed before canopy correction 450 is executed. With reference to FIG. 4, pixel locator 372 determines the location of the pixels from the raw images that will be "superimposed" to form pixel (x,y). Some of the components of pixel locator 372 correct for distortion inherent in the raw images. Other components crop, shift, scale, rotate and perform image correction of the raw images according to the direction of the head of the pilot.

In procedure 412, pixels located at the determined location in procedure 410, i.e., in FIG. 5B, pixels located at position $(I''''_{n(r)}, J''''_{n(r)})$, are read (i.e., retrieved or extracted) from the storage unit. With reference to FIG. 5B, a pixel 458 from image 466 and a pixel 462 from image 468 are read. Each of pixels 458 and 462 are located in positions $(I''''_{n(r)}, J''''_{n(r)})$ in their respective images. It is noted that position $(I''''_{n(r)}, J''''_{n(r)})$ may be different for each raw image, since the determination of the corrected pixel location is executed on each raw image. A pixel 472 represents a read version of pixel 458, and a pixel 474 represents a read version of pixel 462. A pixel 460 in image 466 and a pixel 464 in image 468 are each positioned in position $(I_{n(r)}, J_{n(r)})$ to show the difference between that pixel position and the determined location of the corrected-pixel-position $(I''''_{n(r)}, J''''_{n(r)})$. In this particular example, since no data from image 470 will be projected to the field-of-view of the pilot at pixel $(I_{n(r)}, J_{n(r)})$, no pixels are extracted from image 470. With reference to FIG. 4, pixel extractor 382 then extracts the corresponding pixels and provides them to image processor 386.

In procedure 414, once pixels located at the determined location in procedure 410, i.e., in FIG. 5B, pixels located at position $(I''''_{n(r)}, J''''_{n(r)})$, are read (i.e., retrieved) from the raw images in the storage unit, other neighboring pixels to those pixels are also read from each raw image in the storage unit. For example, three neighboring pixels may be selected. The neighboring pixels can be selected from the following positions relative to the correct location of pixel (x,y): to the right, to the left, above, below, diagonally to the right above, diagonally to the right below, diagonally to the left above and diagonally to the left below. With reference to FIG. 4, once the corrected location of pixel (x,y) is determined, for example pixel (x"",y""), in the raw images, pixel extractor 382 extracts the pixels in the raw images positioned at (x"",y"") and other neighboring pixels from each raw image.

In procedure 416, for each raw image, the pixel location determined in procedure 410, as well as its neighboring pixels, are filtered. The filtering can be executed using a bilinear interpolation, an algorithm that utilizes antialiasing, $\alpha$-$\beta$ filtering, or a combination thereof. For example, if a bilinear interpolation is executed, then the bilinear interpolation determines interpolated grey levels, luminance levels, chrominance levels, or a combination thereof, for the read (i.e., retrieved) pixel location determined in procedure 410 and its neighboring pixels. The bilinear interpolation can be executed for three neighboring pixels by using Equation (6). It is noted that Equation (6) is an example of using a bilinear interpolation with three neighboring pixels. The bilinear interpolation can also be executed with N neighboring pixels. With reference to FIG. 4, in the embodiment of the disclosed technique where neighboring pixels are extracted besides the pixels located at (x"",y"") in each raw image, image processor 386 filters, for each raw image, the pixel located at (x"",y"") as well as its neighboring pixels by a bilinear interpolation. The bilinear interpolation determines interpolated grey levels, luminance levels, chrominance levels, or a combination thereof, for the extracted pixel (x"",y"") and its neighboring pixels.

In procedure 418, the grey levels, luminance levels, chrominance levels, or a combination thereof, of the read (i.e., retrieved) pixels (e.g., transparency, contrast, brightness, gamma correction, filtering, layer level and image preference) are adjusted according to the auxiliary data. The aircraft data received in procedure 400 may be used to adjust the grey levels of the extracted pixels. Since the adjustment to the grey levels of the read pixels includes the layer levels of the read pixels, the read pixels are "superimposed" because their layer levels have been determined. The read pixel with the highest layer level will be the only pixel actually projected to the pilot, thereby giving the pilot the perception of superimposed read pixels. It is noted that in order to provide a stable image projected to the pilot with minimal smearing, vibrations and jitter, it is required that the updating of the extracted pixels be performed at the maximum refresh rate of a projection unit used to project the image to the pilot. The refresh rate of the projection unit should be at least 60 Hz. With reference to FIG. 5B, the grey levels of read pixels 472 and 474 are adjusted, thereby yielding partially grey level adjusted pixels 478 and 476 respectively. Once the respective layer levels of pixels 476 and 478 are determined, and the grey levels of pixels 476 and 478 fully adjusted, pixel 478, which has a higher layer level than pixel 476, is "superimposed" over pixel 476, yielding pixel 480. By manipulating their respective grey levels, pixels 476 and 478 are "superimposed" in a single pixel 480, which is to be projected to position (I,J). With reference to FIG. 4, image processor 386 manipulates the grey levels of the corresponding pixels (e.g., transparency, contrast, brightness, gamma correction, filtering, layer level and image preference) according to the data received from the aircraft data system.

In procedure 420, the "superimposed" pixel (I,J) is projected to the visor of the pilot at position (I,J). In an alternative to procedure 420, the "superimposed" pixel (I,J) is provided to a recording unit, which records and stores an updated image similar to the image projected to the pilot. With reference to FIG. 5B, pixel 480 is projected in an image 482 to the visor of the pilot. Image 482 is the same image as image 446, except that in image 482, a pixel 484 in position (I,J) has been filled with pixel 480. As mentioned before regarding image 446, a section 483 from image 482 is not updated. For purposes of clarity, the not updated section 483 has been omitted from image 482. With reference to FIG. 4, the manipulated pixel with the highest layer level is then projected to the visor of the pilot at the location of (x,y).

It is noted that procedure 420 returns to procedure 408, where another pixel is selected to be projected to the pilot, following the scanning pattern of the projection unit. Procedure 420 continues to return to procedure 408 until all the pixels of a given image are filled. Once all the pixels have been filled, another image, for example a raw camera image, is received, or another image is generated, and updated aircraft data and pilot head data is received. With reference to FIG. 4, once all the pixels forming a complete image have been selected, their corresponding locations in the raw images determined, have been extracted, manipulated and projected to the visor of the pilot, another raw camera image is received, or generated, from the camera or from the image generator, and updated auxiliary data is generated anew in auxiliary data generator 388 and stored in storage unit 384.

It will be appreciated by persons skilled in the art that the disclosed technique is not limited to what has been particularly shown and described hereinabove. Rather the scope of the disclosed technique is defined only by the claims, which follow.

The invention claimed is:

1. Apparatus for displaying at least one image with respect to a line-of-sight (LOS), with substantially no image latency as perceived by a human user, the LOS being determined between the head of a user and at least one coordinate system established in space, said at least one coordinate system and said displayed at least one image being in relative motion there between, the apparatus comprising:

an image source, for providing at least one spatially unregistered image, said at least one spatially unregistered image comprising a plurality of pixels;

a displaying unit, for displaying a spatially registered image on a displaying surface; and a display processor, coupled with said image source and said displaying unit, for spatially registering said at least one spatially unregistered image with said LOS, wherein said display processor comprises:
      a storage unit, for storing said at least one spatially unregistered image;
      an image processor, for iteratively selecting a pixel location on said displaying surface; and
      a pixel locator, coupled with said image processor, for respectively determining in said at least one spatially unregistered image, an unregistered pixel location corresponding to said selected pixel location on said displaying surface, wherein a pixel stored in said unregistered pixel location represents a spatially registered pixel in said selected pixel location on said displaying surface, wherein for each selected pixel location on said displaying surface, said display processor extracting said pixel stored in said unregistered pixel location and providing said pixel stored in said unregistered pixel location to said displaying unit, said displaying unit displaying said pixel stored in said unregistered pixel location in said selected pixel location on said displaying surface, and wherein for each said spatially registered image, at least one of said pixel stored in said unregistered pixel location extracted by said display processor being displayed by said displaying unit before at least another one of said pixel stored in said unregistered pixel location is extracted by said display processor, thereby displaying said at least one image with respect to said LOS with substantially no image latency as perceived by said human user as said displaying unit iteratively displays respective pixels in each said selected pixel location on said displaying surface.

2. The apparatus according to claim 1, wherein said LOS is updated in real-time.

3. The apparatus according to claim 1, wherein said at least one coordinate system is established in a real space.

4. The apparatus according to claim 1, wherein said at least one coordinate system is established in a virtual space.

5. The apparatus according to claim 1, wherein said image processor adjusts the grey levels of said pixel stored in said unregistered pixel location before said displaying unit displays said pixel stored in said unregistered pixel location in said selected pixel location on said displaying surface.

6. The apparatus according to claim 1, wherein said image processor adjusts the luminance levels of said pixel stored in said unregistered pixel location before said displaying unit displays said pixel stored in said unregistered pixel location in said selected pixel location on said displaying surface.

7. The apparatus according to claim 1, wherein said image processor adjusts the chrominance levels of said pixel stored in said unregistered pixel location before said displaying unit displays said pixel stored in said unregistered pixel location in said selected pixel location on said displaying surface.

8. The apparatus according to claim 5, wherein said image processor adjusts said grey levels using at least one of α-β filtering and at least one antialiasing algorithm.

9. The apparatus according to claim 6, wherein said image processor adjusts said luminance levels using at least one of α-β filtering and at least one antialiasing algorithm.

10. The apparatus according to claim 7, wherein said image processor adjusts said chrominance levels using at least one of α-β filtering and at least one antialiasing algorithm.

11. The apparatus according to claim 1, further comprising a recording unit, coupled with said display processor, for recording said displayed pixel stored in said unregistered pixel location in said selected pixel location on said displaying surface.

12. The apparatus according to claim 1, wherein said displaying surface is selected from the list consisting of:
an optical visor viewable by at least one eye of said user;
a helmet mounted display;
a heads-up display;
a heads-down display;
a virtual heads-up display; and
a virtual multi-function display.

13. The apparatus according to claim 1, wherein said pixel locator comprises a visor distortion corrector for determining said unregistered pixel location corresponding to said selected pixel location on said displaying surface in accordance with distortion inherent in an optical visor used as a displaying surface.

14. The apparatus according to claim 13, wherein said visor distortion corrector determines said unregistered pixel location, according to at least one operation selected from the list consisting of:
a known polynomial which accounts for said distortion inherent in said optical visor;
a look-up table; and
a function which allows said unregistered pixel location to be determined.

15. The apparatus according to claim 1, wherein said image source is selected from the list consisting of:
a camera;
an auxiliary data generator; and
an image generator.

16. The apparatus according to claim 1, wherein said pixel locator comprises a camera distortion corrector for determining said unregistered pixel location, corresponding to said selected pixel location on said displaying surface, in said at least one spatially unregistered image received from a camera in accordance with distortion inherent in the optics of said camera.

17. The apparatus according to claim 16, wherein said camera distortion corrector determines said unregistered pixel location corresponding to said selected pixel location on said displaying surface, according to at least one operation selected from the list consisting of:
a known polynomial which accounts for said distortion inherent in the optics of said camera in said at least one spatially unregistered image received from said camera;
a look-up table; and
a function which allows said unregistered pixel location to be determined.

18. The apparatus according to claim 1, wherein said image source is a camera selected from the list consisting of:
an IR camera;
a visible light camera;
an ICCD camera;
an image intensified camera;
a sensor fused camera; and
an aircraft panoramic night vision system.

19. The apparatus according to claim 1, wherein said image source is an image generator that generates at least one virtual reality image.

20. The apparatus according to claim 1, further comprising a head sensor, coupled with said display processor, for determining the position of the head of said user, relative to said at least one coordinate system.

21. The apparatus according to claim 20, wherein said LOS is updated according to a most up-to-date determining of said position of said head of said user.

22. The apparatus according to claim 20, wherein said position comprises the location and the orientation of the head of said user.

23. The apparatus according to claim 20, wherein said pixel locator comprises a head line-of-sight corrector for determining said unregistered pixel location corresponding to said selected pixel location on said displaying surface in accordance with said determined position of the head of said user.

24. The apparatus according to claim 23, wherein said head line-of-sight corrector determines said unregistered pixel location corresponding to said selected pixel location on said displaying surface, according to at least one operation selected from the list consisting of:
an equation using at least one scaling factor;
an equation using at least one shifting factor;
an equation using at least one rotation factor;
an equation using at least one cropping parameter;
an Euler correction;
a polynomial approximation;
an algorithm using a prediction of the position of the head of said user; and
a spatial filter of said at least one spatially unregistered image.

25. The apparatus according to claim 23, wherein said head line-of-sight corrector determines said unregistered pixel location corresponding to said selected pixel location on said displaying surface in accordance with said determined position of the head of said user for at least one eye of said user.

26. The apparatus according to claim 1, wherein said at least one spatially unregistered image is selected from the list consisting of:
   an IR camera image;
   a visible light camera image;
   an ICCD camera image;
   an image intensified camera image;
   an aircraft panoramic night vision system image;
   a VHUD image;
   a VMFD image;
   a virtual reality image;
   a virtual world image;
   static symbology;
   dynamic symbology;
   a digital map;
   a weapons camera image;
   a weapons view image;
   a target zoom camera;
   an HMD day camera image;
   an HMD night camera image;
   three-dimensional video input; and
   internal calibration patterns.

27. The apparatus according to claim 1, wherein said image processor retrieves at least one neighbor pixel of said pixel stored in said unregistered pixel location from said at least one spatially unregistered image stored is said storage unit.

28. The apparatus according to claim 27, wherein said image processor filters a retrieved one of said pixel stored in said unregistered pixel location and said retrieved at least one neighbor pixel using a bilinear interpolation.

29. The apparatus according to claim 28, wherein said bilinear interpolation is executed using the expression $$\text{Grey\_level}(x'''',y'''')=A(1-\Delta x)(1-\Delta y)+B(\Delta x)(1-\Delta y)+C(1-\Delta x)(\Delta y)+D(\Delta x)(\Delta y)$$

wherein Grey_level(x'''', y'''') is the interpolated grey levels for said retrieved one of said pixel stored in said unregistered pixel location, A is the current grey level of said retrieved one of said pixel stored in said unregistered pixel location, B, C and D are respectively the grey levels of a first, second and third retrieved at least one neighbor pixel of said retrieved one of said pixel stored in said unregistered pixel location, and $\Delta x$ and $\Delta y$ are subpixel information for said retrieved one of said pixel stored in said unregistered pixel location.

30. The apparatus according to claim 27, wherein said image processor filters a retrieved one of said pixel stored in said unregistered pixel location and said retrieved at least one neighbor pixel using antialiasing.

31. The apparatus according to claim 1, further comprising an aircraft data system, coupled with said display processor, for determining the position of an aircraft mounted with said apparatus.

32. The apparatus according to claim 31, wherein said aircraft data system monitors data determined by aviation systems related to said aircraft.

33. The apparatus according to claim 1, wherein said pixel locator comprises a canopy distortion corrector for determining said unregistered pixel location corresponding to said selected pixel location on said displaying surface in accordance with distortion inherent in a canopy of a vehicle.

34. The apparatus according to claim 33, wherein canopy distortion corrector determines said unregistered pixel location corresponding to said selected pixel location on said displaying surface, according to said at least one operation selected from the list consisting of:
   a known polynomial which accounts for said distortion inherent in said canopy;
   a look-up table; and
   a function which allows said unregistered pixel location to be determined.

35. Method for displaying at least one image with respect to a line-of-sight (LOS), with substantially no image latency as perceived by a human user, the LOS being determined between the head of a user and at least one coordinate system established in space, said at least one coordinate system and said displayed at least one image being in relative motion there between, the method comprising the procedures of:
   providing at least one spatially unregistered image, from an image source, said at least one spatially unregistered image comprising a plurality of pixels;
   storing said at least one spatially unregistered image;
   iteratively selecting a pixel location on a displaying surface;
   respectively determining in said at least one spatially unregistered image an unregistered pixel location corresponding to said selected pixel location on said displaying surface; and
   for each selected pixel location on said displaying surface, extracting a pixel stored in said unregistered pixel location and displaying said pixel stored in said unregistered pixel location in said selected pixel location on said displaying surface,
   wherein said pixel stored in said unregistered pixel location represents a spatially registered pixel in said selected pixel location on said displaying surface, and
   wherein for said displayed at least one image, at least one of said pixel stored in said unregistered pixel location is extracted and displayed in said respective selected pixel location on said displaying surface before at least another one of said pixel stored in said unregistered pixel location is extracted,
   thereby displaying said at least one image with respect to said LOS with substantially no image latency as perceived by said human user as pixels are respectively displayed in each said selected pixel location on said displaying surface.

36. The method according to claim 35, further comprising the procedure of updating said LOS in real-time.

37. The method according to claim 35, wherein said at least one coordinate system is established in a real space.

38. The method according to claim 35, wherein said at least one coordinate system is established in a virtual space.

39. The method according to claim 35, further comprising the procedure of adjusting the grey levels of said pixel stored in said unregistered pixel location before said procedure of displaying.

40. The method according to claim 35, further comprising the procedure of adjusting the luminance levels of said pixel stored in said unregistered pixel location before said procedure of displaying.

41. The method according to claim 35, further comprising the procedure of adjusting the chrominance levels of said pixel stored in said unregistered pixel location before said procedure of displaying.

42. The method according to claim 39, wherein said procedure of adjusting said grey levels is executed using at least one of $\alpha$-$\beta$ filtering and at least one antialiasing algorithm.

43. The method according to claim 40, wherein said procedure of adjusting said luminance levels is executed using at least one of $\alpha$-$\beta$ filtering and at least one antialiasing algorithm.

44. The method according to claim 41, wherein said procedure of adjusting said chrominance levels is executed using at least one of α-β filtering and at least one antialiasing algorithm.

45. The method according to claim 35, further comprising the procedure of recording said pixel stored in said unregistered pixel location displayed in said selected pixel location on said displaying surface.

46. The method according to claim 35, wherein said displaying surface is selected from the list consisting of:
- an optical visor viewable by at least one eye of said user;
- a helmet mounted display;
- a heads-up display;
- a heads-down display;
- a virtual heads-up display; and
- a virtual multi-function display.

47. The method according to claim 35, wherein said procedure of respectively determining comprises determining said unregistered pixel location corresponding to said selected pixel location on said displaying surface in accordance with at least one type of distortion, said at least one type of distortion selected from the list consisting of:
- optical visor distortion inherent in an optical visor;
- vehicle canopy distortion inherent in the canopy of a vehicle;
- camera distortion inherent in the optics of a camera; and
- head LOS distortion.

48. The method according to claim 47, wherein said procedure of respectively determining comprises determining said unregistered pixel location corresponding to said selected pixel location on said displaying surface in accordance with said optical visor distortion, according to at least one operation selected from the list consisting of:
- a known polynomial which accounts for said inherent distortion in said optical visor;
- a look-up table; and
- a function which allows said unregistered pixel location to be determined.

49. The method according to claim 47, wherein said procedure of respectively determining comprises determining said unregistered pixel location corresponding to said selected pixel location on said displaying surface in accordance with said camera distortion in said at least one spatially unregistered image received from a camera, according to at least one operation selected from the list consisting of:
- a known polynomial which accounts for said camera distortion in said at least one spatially unregistered image received from said camera;
- a look-up table; and
- a function which allows said unregistered pixel location to be determined.

50. The method according to claim 47, further comprising the procedure of determining the position of the head of said user, relative to said at least one coordinate system.

51. The method according to claim 50, further comprising the procedure of updating said LOS according to a most up-to-date determining of said position of said head of said user.

52. The method according to claim 50, wherein said position comprises the location and the orientation of the head of said user.

53. The method according to claim 50, wherein said procedure of respectively determining comprises determining said unregistered pixel location corresponding to said selected pixel location on said displaying surface in accordance with said head LOS distortion and the determined position of the head of said user, according to at least one operation selected from the list consisting of:
- an equation using at least one scaling factor;
- an equation using at least one shifting factor;
- an equation using at least one rotation factor;
- an equation using at least one cropping parameter;
- an Euler correction;
- a polynomial approximation;
- an algorithm using a prediction of the position of the head of said user; and
- a spatial filter of said at least one spatially unregistered image.

54. The method according to claim 50, wherein said procedure of respectively determining comprises determining said unregistered pixel location corresponding to said selected pixel location on said displaying surface in accordance with said head LOS distortion and the determined position of the head of said user for at least one eye of said user.

55. The method according to claim 35, wherein said at least one spatially unregistered image is selected from the list consisting of:
- an IR camera image;
- a visible light camera image;
- an ICCD camera image;
- an image intensified camera image;
- an aircraft panoramic night vision system image;
- a VHUD image;
- a VMFD image;
- a virtual reality image;
- a virtual world image;
- static symbology;
- dynamic symbology;
- a digital map;
- a weapons camera image;
- a weapons view image;
- a target zoom camera;
- an HMD day camera image;
- an HMD night camera image;
- three-dimensional video input; and
- internal calibration patterns.

56. The method according to claim 35, further comprising the procedure of reading at least one neighbor pixel of said stored pixel in said unregistered pixel location from said stored at least one spatially unregistered image.

57. The method according to claim 56, further comprising the procedure of filtering a read one of said stored pixel in said unregistered pixel location and said read at least one neighbor pixel using a bilinear interpolation.

58. The method according to claim 57, wherein said bilinear interpolation is executed using the expression $$\text{Grey\_level}(x'''',y'''')=A(1-\Delta x)(1-\Delta y)+B(\Delta x)(1-\Delta y)+C(1-\Delta x)(\Delta y)+D(\Delta x)(\Delta y)$$

wherein Grey_level(x'''',y'''') is the interpolated grey levels for said read one of said stored pixel in said unregistered pixel location, A is the current grey level of said read one of said stored pixel in said unregistered pixel location, B, C and D are respectively the grey levels of a first, second and third read at least one neighbor pixel of said read one of said pixel stored in said unregistered pixel location, and $\Delta x$ and $\Delta y$ are subpixel information for said read one of said pixel stored in said unregistered pixel location.

59. The method according to claim 56, further comprising the procedure of filtering a read one of said stored pixel in said unregistered pixel location and said read at least one neighbor pixel using antialiasing.

60. The method according to claim 35, further comprising the procedure of determining the position of an aircraft.

61. The method according to claim 60, further comprising the procedure of monitoring data determined by aviation systems related to said aircraft.

62. The method according to claim 47, wherein said procedure of respectively determining comprises determining said unregistered pixel location corresponding to said selected pixel location on said displaying surface in accordance with said vehicle canopy distortion, according to said at least one operation selected from the list consisting of:
- a known polynomial which accounts for said vehicle canopy distortion;
- a look-up table; and
- a function which allows said unregistered pixel location to be determined.

* * * * *